(12) United States Patent
Tummala et al.

(10) Patent No.: US 9,504,754 B2
(45) Date of Patent: Nov. 29, 2016

(54) CURCUMINOID COMPLEXES WITH ENHANCED STABILITY, SOLUBILITY AND/OR BIOAVAILABILITY

(71) Applicant: South Dakota Board of Regents, Brookings, SD (US)

(72) Inventors: Hemachand Tummala, Brookings, SD (US); Sunny Kumar, Brookings, SD (US)

(73) Assignee: South Dakota Board of Regents, Brookings, SD (US)

( * ) Notice: Subject to any disclaimer, the term of this patent is extended or adjusted under 35 U.S.C. 154(b) by 0 days.

(21) Appl. No.: 14/213,063

(22) Filed: Mar. 14, 2014

(65) Prior Publication Data
US 2014/0271530 A1 Sep. 18, 2014

Related U.S. Application Data

(60) Provisional application No. 61/794,967, filed on Mar. 15, 2013.

(51) Int. Cl.
*A61K 47/48* (2006.01)
*A61K 31/12* (2006.01)

(52) U.S. Cl.
CPC ......... *A61K 47/48176* (2013.01); *A61K 31/12* (2013.01)

(58) Field of Classification Search
CPC ........................ A61K 47/48176; A61K 31/12
See application file for complete search history.

(56) References Cited

U.S. PATENT DOCUMENTS

| | | | |
|---|---|---|---|
| 7,070,814 B2 | 7/2006 | Qazi et al. | |
| 7,780,873 B2 | 8/2010 | Mora-Gutierrez et al. | |
| 2007/0243233 A1 | 10/2007 | Cherukuri et al. | |
| 2009/0143433 A1 | 6/2009 | Hendrix | |
| 2010/0197584 A1 | 8/2010 | Banerjee et al. | |
| 2011/0034564 A1 | 2/2011 | Parkkinen | |
| 2011/0171308 A1* | 7/2011 | Zhang et al. | 424/487 |
| 2011/0305765 A1 | 12/2011 | Mathur et al. | |

FOREIGN PATENT DOCUMENTS

| | | |
|---|---|---|
| EP | 2 229 940 A1 | 9/2010 |
| WO | WO 2009/101263 A2 | 8/2009 |
| WO | WO 2009/121069 A2 | 10/2009 |
| WO | WO 2010/033692 A1 | 3/2010 |
| WO | WO 2010/106191 A1 | 9/2010 |
| WO | WO 2011/101859 A1 | 8/2011 |
| WO | WO 2011/142795 A9 | 11/2011 |
| WO | WO 2012/024405 A2 | 2/2012 |
| WO | WO2012/049253 * | 4/2012 ............. A23L 1/015 |
| WO | WO 2012/142511 A2 | 10/2012 |

OTHER PUBLICATIONS

EUDRAGIT Brochure.*
"Abstract for TR-427—Turmeric Oleoresin (CASRN 8024-37-1) Toxicology and Carcinogenesis Studies of Turmeric Oleoresin (CAS No. 8024-37-1) (Major Component 79%-85% Curcumin, CAS No. 458-37-7) in F344/N Rats and B6C3F₁ Mice (Feed Studies)," National Toxicology Program, Aug. 1993, 4 pages.
Aggarwal et al., "Curcumin (Diferuloylmethane) Down-Regulates Expression of Cell Proliferation and Antiapoptotic and Metastatic Gene Products through Suppression of IκBα Kinase and Akt Activation," Molecular Pharmacology, vol. 69, No. 1, 2006, pp. 195-206.
Aggarwal et al., "Curcumin Suppresses the Paclitaxel-Induced Nuclear Factor-κB Pathway in Breast Cancer Cells and Inhibits Lung Metastasis Of Human Breast Cancer in Nude Mice," Clinical Cancer Research, vol. 11, No. 20, Oct. 15, 2005, pp. 7490-7498.
Aggarwal et al., "Potential Therapeutic Effects of Curcumin, the Anti-inflammatory Agent, Against Neurodegenerative, Cardiovascular, Pulmonary, Metabolic, Autoimmune and Neoplastic Diseases," International Journal of Biochemical Cell Biology, vol. 41, No. 1, 2009, pp. 40-59.
Aggarwal et al., "Targeting Signal-Transducer-and—Activator-of-Transcription-3 for Prevention and Therapy of Cancer: Modern Target but Ancient Solution," Annals of the New York Academy of Sciences, vol. 1091, 2006, pp. 151-169.
Ammon et al., "Pharmacology of *Curcuma longa*," Planta Medica, vol. 57, 1991, pp. 1-7.
Anand et al., "Biological activities of curcumin and its analogues (Congeners) made by man and Mother Nature," Biochemical Pharmacology, vol. 76, 2008, pp. 1590-1611.
Arbiser et al., "Curcumin Is an In Vivo Inhibitor of Angiogenesis," Molecular Medicine, vol. 4, 1998, pp. 376-383.
Bachmeier et al., "The Chemopreventive Polyphenol Curcumin Prevents Hematogenous Breast Cancer Metastases in Immunodeficient Mice," Cellular Physiology and Biochemistry, vol. 19, 2007, pp. 137-152.
Bae et al., "Curcumin inhibits hypoxia-induced angiogenesis via down-regulation of HIF-1," Oncology Reports, vol. 15, 2006, pp. 1557-1562.
Balasubramanyam et al., "Curcumin, a Novel p300/CREB-binding Protein-specific Inhibitor of Acetyltransferase, Represses the Acetylation of Histone/Nonhistone Proteins and Histone Acetyltransferase-dependent Chromatin Transcription," The Journal of Biological Chemistry, vol. 279, No. 49, Dec. 3, 2004, pp. 51163-51171.

(Continued)

*Primary Examiner* — Sean Basquill
(74) *Attorney, Agent, or Firm* — Patterson Thuente Pedersen, P.A.

(57) ABSTRACT

Methods and materials relating to a medicament preparation comprising a curcuminoid component and a euradit component provided as a curcuminoid-eudragit complex, which enhance the bioavailability of the curcumin component and are useful for the treatment of various diseases including cancer, neurodegeneration, inflammation, and immunodeficiency. In some aspects, the curcuminoid component comprises curcumin to prepare a curcumin-eudragit complex and a medicament comprising curcumin-eudragit complexes.

24 Claims, 11 Drawing Sheets

(56) References Cited

OTHER PUBLICATIONS

Balogun et al., "Curcumin activates the haem oxygenase-1 gene via regulation of Nrf2 and the antioxidant-responsive element," Biochemical Journal, vol. 371, 2003, pp. 887-895.

Bannerjee et al., "Anti-Inflammatory and Growth-Stimulating Effects Precede Nutritional Restitution During Enteral Feeding in Crohn Disease," Journal of Pediatric Gastroenterology and Nutrition, vol. 38, Mar. 2004, pp. 270-275.

Bharti et al., "Curcumin (Diferuloylmethane) Inhibits Constitutive and IL-6-Inducible STAT3 Phosphorylation in Human Multiple Myeloma Cells," The Journal of Immunology, vol. 171, 2003, pp. 3863-3871.

Bhawana et al., "Curcumin Nanoparticles: Preparation, Characterization, and Antimicrobial Study," Journal of Agriculture and Food Chemistry, vol. 59, 2011, pp. 2056-2061.

Billerey-Larmonier et al., "Protective Effects of Dietary Curcumin in Mouse Model of Chemically Induced Colitis Are Strain Dependent," Inflammatory Bowel Diseases, vol. 14, No. 6, 2008, pp. 780-793.

Binion et al., "Curcumin inhibits VEGF-mediated angiogenesis in human intestinal microvascular endothelial cells through COX-2 and MAPK inhibition," Gut, vol. 57, 2008, pp. 1509-1517.

Brooks et al., "Ubiquitination, phosphorylation and acetylation: the molecular basis for p53 regulation," Current Opinion in Cell Biology, vol. 15, 2003, pp. 164-171.

Bundy et al., "Turmeric Extract May Improve Irritable Bowel Syndrome Symptomology in Otherwise Healthy Adults: A Pilot Study," The Journal of Alternative and Complementary Medicine, vol. 10, No. 6, 2004, pp. 1015-1018.

Chainani-Wu, "Safety and Anti-Inflammatory Activity of Curcumin: A Component of Tumeric (*Curcuma longa*)," The Journal of Alternative and Complementary Medicine, vol. 9, No. 1, 2003, pp. 161-168.

Chen et al., "Activation of PPARγ by curcumin inhibits Moser cell growth and mediates suppression of gene expression of cyclin D1 and EGFR," American Journal of Physiology—Gastrointestinal and Liver Physiology, vol. 288, 2005, pp. G447-G456.

Chen et al., "Curcumin, both Histone Deacetylase and p300/CBP-Specific Inhibitor, Represses the Activity of Nuclear Factor Kappa B and Notch 1 in Raji Cells," Basic & Clinical Pharmacology & Toxicology, vol. 101, 2007, pp. 427-433.

Chen et al., "Inhibition of the c-Jun N-terminal kinase (JNK) signaling pathway by curcumin," Oncogene, vol. 17, 1998, pp. 173-178.

Choudhuri et al., "Curcumin Selectively Induces Apoptosis in Deregulated Cyclin D1-expressed Cells at $G_2$ Phase of Cell Cycle in a p53-dependent Manner," The Journal of Biological Chemistry, vol. 280, No. 20, May 20, 2005, pp. 20059-20068.

Chuang et al., "Inhibition by curcumin of diethylnitrosamine-induced hepatic hyperplasia, inflammation, cellular gene products and cell-cycle-related proteins in rats," Food and Chemical Toxicology, vol. 38, 2000, pp. 991-995.

Claramunt et al., "Synthesis and biological evaluation of curcuminoid pyrazoles as new therapeutic agents in inflammatory bowel disease: Effect on matrix metalloproteinases," Bioorganic & Medicinal Chemistry, vol. 17, 2009, pp. 1290-1296.

Cohen et al., "Suppression of Interleukin 6 and 8 Production in Head and Neck Cancer Cells with Curcumin via Inhibition of IκB Kinase," Archives of Otolaryngology—Head & Neck Surgery, vol. 135, No. 2, Feb. 2009, pp. 190-197.

Collett et al., "Curcumin induces c-jun N-terminal kinase-dependent apoptosis in HCT116 human colon cancer cells," Carcinogenesis, vol. 25, No. 11, 2004, pp. 2183-2189.

Collett et al., "Curcumin modifies Apc$^{min}$ apoptosis resistance and inhibits 2-amino 1-methyl-6-phenylimidazo[4,5-b]pyridine (PhIP) induced tumour formation in Apc$^{min}$ mice," Carcinogenesis, vol. 22, No. 5, 2001, pp. 821-825.

Cruz-Correa et al., "Combination Treatment With Curcumin and Quercetin of Adenomas in Familial Adenomatous Polyposis," Clinical Gastroenterology and Hepatology, vol. 4, 2006, pp. 1035-1038.

Devasena et al., "Prevention of 1,2-dimethylhydrazine-induced circulatory oxidative stress by bis-1,7-(2-hy-droxyphenyl)-hepta-1,6-diene-3,5-dione during colon carcinogenesis," Pharmacological Reports, vol. 58, 2006, pp. 229-235.

Dhillon et al., "Phase II Trial of Curcumin in Patients with Advanced Pancreatic Cancer," Clinical Cancer Research, vol. 14, No. 14, Jul. 15, 2008, pp. 4491-4499.

Epstein et al., "Curcumin as a therapeutic agent: the evidence from in vitro, animal and human studies," British Journal of Nutrition, vol. 103, 2010, pp. 1545-1557.

Fisher et al., "Tamoxifen for Prevention of Breast Cancer: Report of the National Surgical Adjuvant Breast and Bowel Project P-1 Study," Journal of the National Cancer Institute, vol. 90, No. 18, Sep. 16, 1998, pp. 1371-1388.

Fujio et al., "Signals Through gp130 Upregulate bcl-x Gene Expression Via STAT1-binding cis-Element in Cardiac Myocytes," Journal of Clinical Investigation, vol. 99, No. 12, Jun. 1997, pp. 2898-2905.

Garcea et al., "Consumption of the Putative Chemopreventive Curcumin by Cancer Patients: Assessment of Curcumin Levels in the Colorectum and their Pharmacodynamic Consequences," Cancer Epidemiology, Biomarkers & Prevention, vol. 14, No. 1, 2005, pp. 120-125.

Goh et al., "Inflammatory bowel disease: A survey of the epidemiology in Asia," Journal of Digestive Diseases, vol. 10, 2009, pp. 1-6.

Han et al., "Curcumin Causes the Growth Arrest and Apoptosis of B Cell Lymphoma by Downregulation of egr-1, C-myc, Bcl-$X_L$, NF-κB, and p53," Clinical Immunology, vol. 93, No. 2, Nov. 1999, pp. 152-161.

Hanai et al., "Curcumin Maintenance Therapy for Ulcerative Colitis: Randomized, Multicenter, Double-Blind, Placebo-Controlled Trial," Clinical Gastroenterology and Hepatology, vol. 4, 2006, pp. 1502-1506.

Hecht et al., "Evaluation of butylated hydroxyanisole, myo-inositol, curcumin, esculetin, resveratrol and lycopene as inhibitors of benzo[α]pyrene plus 4-(methylnitrosamino)-1-(3-pyridyl)-1-butanone-induced lung tumorigenesis in A/J mice," Cancer letters, vol. 137, 1999, pp. 123-130.

Heng et al., "Drug-induced suppression of phosphorylase kinase activity correlates with resolution of psoriasis as assessed by clinical, histological and immunohistochemical parameters," British Journal of Dermatology, vol. 143, 2000, No. 937-949.

Heuschkel et al., "Enteral Nutrition and Corticosteroids in the Treatment of Acute Crohn's Disease in Children," Journal of Pediatric Gastroenterology and Nutrition, vol. 31, No. 1, Jul. 2000, pp. 8-15.

Holt et al., "Curcumin Therapy in Inflammatory Bowel Disease: A Pilot Study," Digestive Diseases and Sciences, vol. 50, No. 11, Nov. 2005, pp. 2191-2193.

Hu et al., "Proapoptotic effect of curcumin on human neutrophils: Activation of the p38 mitogen-activated protein kinase pathway," Critical Care Medicine, vol. 33, No. 11, 2005, pp. 2571-2578.

Huang et al., "Effect of dietary curcumin and dibenzoylmethane on formation of 7,12-dimethylbenz[α]anthracene-induced mammary tumors and lymphomas/leukemias in Sencar mice," Carcinogenesis, vol. 19, No. 9, 1998, pp. 1697-1700.

Huang et al., "Inhibitory Effect of Curcumin, Chlorogenic Acid, Caffeic Acid, and Ferulic Acid on Tumor Promotion in Mouse Skin by 12-0-Tetradecanoylphorbol-13-acetate," Cancer Research, vol. 48, Nov. 1, 1988, pp. 5941-5946.

Huang et al., "Inhibitory Effects of Dietary Curcumin on Forestomach, Duodenal, and Colon Carcinogenesis in Mice," Cancer Research, vol. 54, Nov. 15, 1994, pp. 5841-5847.

Huang et al., "Inhibitory effects of topical application of low doses of curcumin on 12-O-tetradecanoylphorbol-13-acetate-induced tumor promotion and oxidized DNA bases in mouse epidermis," Carcinogenesis, vol. 18. No. 1, 1997, pp. 83-88.

Hussain et al., "Curcumin induces apoptosis via inhibition of PI3'-kinase/AKT pathway in Acute T cell Leukemias," Apoptosis, vol. 11, 2006, pp. 245-254.

Inano et al., "Chemoprevention by curcumin during the promotion stage of tumorigenesis of mammary gland in rats irradiated with γ-rays," Carcinogenesis, vol. 20, No. 6, 1999, pp. 1011-1018.

(56) References Cited

OTHER PUBLICATIONS

Iqbal et al., "Curcumin attenuates oxidative damage in animals treated with a renal carcinogen, ferric nitrilotriacetate (Fe-NTA): implications for cancer prevention," Molecular and Cellular Biochemistry, vol. 324, 2009, pp. 157-164.
Jian et al., "Preventive and therapeutic effects of NF-kappaB inhibitor curcumin in rats colitis induced by trinitrobenzene sulfonic acid," World Journal of Gastroenterology, vol. 11, No. 12, 2005, pp. 1747-1752.
Kawamori et al., "Chemopreventive Effect of Curcumin, a Naturally Occurring Anti-Inflammatory Agent, during the Promotion/Progression Stages of Colon Cancer," Cancer Research, vol. 59, Feb. 1, 1999, pp. 597-601.
Kidd, "Bioavailability and Activity of Phytosome Complexes from Botanical Polyphenols: The Silymarin, Curcumin, Green Tea, and Grape Seed Extracts," Alternative Medicine Review, vol. 14, No. 3, 2009, pp. 226-246.
Kim et al., "Chemopreventive effects of carotenoids and curcumins on mouse colon carcinogenesis after 1,2-dimethylhydrazine initiation," Carcinogenesis, vol. 19, No. 1, 1998, pp. 81-85.
Kim et al., "Pharmacological Doses of Dietary Curcumin increase Colon Epithelial Cell Proliferation In Vivo in Rats," Phytotherapy Research, vol. 21, 2007, pp. 995-998.
Kobelt, "Health economic issues in rheumatoid arthritis," Scandinavian Journal of Rheumatology, vol. 35, 2006, pp. 415-425.
Kunnumakkara et al., "Curcumin Potentiates Antitumor Activity of Gemcitabine in an Orthotopic Model of Pancreatic Cancer through Suppression of Proliferation, Angiogenesis, and Inhibition of Nuclear Factor-κB—Regulated Gene Products," Cancer Research, vol. 67, No. 8, Apr. 15, 2007, pp. 3853-3861.
Kwon et al., "Inhibition of Colonic Aberrant Crypt Foci by Curcumin in Rats Is Affected by Age," Nutrition and Cancer, vol. 48, No. 1, 2004, pp. 37-43.
Kwon et al., "Effect of azoxymethane and curcumin on transcriptional levels of cyclooxygenase-1 and -2 during initiation of colon carcinogenesis," Scandinavian Journal of Gastroenterology, vol. 42, 2007, pp. 72-80.
Lal et al., "Role of Curcumin in Idiopathic Inflammatory Orbital Pseudotumours," Phytotherapy Research, vol. 14, 2000, pp. 443-447.
Lao et al., "Dose escalation of a curcuminoid formulation," BMC Complementary and Alternative Medicine, vol. 6, No. 10, 2006, 4 pages.
Larmonier et al., "Limited effects of dietary curcumin on Th-1 driven colitis in IL-10 deficient mice suggest an IL-10-dependent mechanism of protection," American Journal of Physiology—Gastrointestinal and Liver Physiology, vol. 295, No. 5, Nov. 2008, pp. G1079-G1091.
Lee et al., "Transcriptional Regulation of VCAM-1 Expression by Tumor Necrosis Factor-α in Human Tracheal Smooth Muscle Cells: Involvement of MAPKs, NF-κB, p300, and Histone Acetylation," Journal of Cellular Physiology, vol. 207, 2006, pp. 174-186.
Li et al., "Liposome-Encapsulated Curcumin: In Vitro and In Vivo Effects on Proliferation, Apoptosis, Signaling, and Angiogenesis," Cancer, vol. 104, No. 6, Sep. 15, 2005, pp. 1322-1331.
Li et al., "Liposomal curcumin with and without oxaliplatin: effects on cell growth, apoptosis, and angiogenesis in colorectal cancer," Molecular Cancer Therapeutics, vol. 6, No. 4, Apr. 2007, pp. 1276-1283.
Liang et al., "Inhibition of LPS-induced production of inflammatory factors in the macrophages by mono-carbonyl analogues of curcumin," Journal of Cellular Molecular Medicine, vol. 13, No. 9B, 2009, pp. 3370-3379.
Liao et al., "Curcumin induces apoptosis through an ornithine decarboxylase-dependent pathway in human promyelocytic leukemia HL-60 cells," Life Sciences, vol. 82, 2008, pp. 367-375.
Limtrakul et al., "Inhibitory effect of dietary curcumin on skin carcinogenesis in mice," Cancer Letters, vol. 116, 1997, pp. 197-203.

Lin et al., "Curcumin Inhibits Tumor Growth and Angiogenesis in Ovarian Carcinoma by Targeting the Nuclear Factor-κB Pathway," Clinical Cancer Research, vol. 13, No. 11, Jun. 1, 2007, pp. 3423-3430.
Lin et al., "Inhibition by dietary dibenzoylmethane of mammary gland proliferation, formation of DMBA-DNA adducts in mammary glands, and mammary tumorigenesis in Sencar mice," Cancer letters, vol. 168, 2001, pp. 125-132.
LoTempio et al., "Curcumin Suppresses Growth of Head and Neck Squamous Cell Carcinoma," Clinical Cancer Research, vol. 11, No. 19, Oct. 1, 2005, pp. 6994-7002.
Mackenzie et al., "Curcumin induces cell-arrest and apoptosis in association with the inhibition of constitutively active NF-κB and STAT3 pathways in Hodgkin's lymphoma cells," International Journal of Cancer, vol. 123, 2008, pp. 56-65.
Manoharan et al., "Chemopreventive efficacy of curcumin and piperine during 7,12-dimethylbenz [a]anthracene-induced hamster buccal pouch carcinogenesis," Singapore Medical Journal, vol. 50, No. 2, 2009, pp. 139-146.
Monteleone et al., "Post-transcriptional Regulation of Smad7 in the Gut of Patients With Inflammatory Bowel Disease," Gastroenterology, vol. 129, 2005, pp. 1420-1429.
Moos et al., "Curcumin impairs tumor suppressor p53 function in colon cancer cells," Carcinogenesis, vol. 25, No. 9, 2004, pp. 1611-1617.
Naito et al., "The Protective Effects of Tetrahydrocurcumin on Oxidative Stress In Cholesterol-fed Rabbits," Journal of Atherosclerosis and Thrombosis, vol. 9, No. 5, 2002, pp. 243-250.
Nakamura et al., "Conjugated linoleic acid isomers' roles in the regulation of PPAR-γ and NF-κB DNA binding and subsequent expression of antioxidant enzymes in human umbilical vein endothelial cells," Nutrition, vol. 25, 2009, pp. 800-811.
Narayanan et al., "Liposome encapsulation of curcumin and resveratrol in combination reduces prostate cancer incidence in PTEN knockout mice," International Journal of Cancer, vol. 125, 2009, pp. 1-8.
Nones et al., "Multidrug resistance gene deficient ($mdr1\alpha^{-/-}$) mice have an altered caecal microbiota that precedes the onset of intestinal inflammation," Journal of Applied Microbiology, vol. 107, 2009, pp. 557-566.
Odot et al., "In Vitro and In Vivo Anti-Tumoral Effect of Curcumin Against Melanoma Cells," International Journal of Cancer, vol. 111, 2004, pp. 381-387.
Okada et al., "Curcumin and Especially Tetrahydrocurcumin Ameliorate Oxidative Stress-Induced Renal Injury in Mice," The Journal of Nutrition, vol. 131, No. 8, Aug. 2001, pp. 2090-2095.
Okazaki et al., "Suppressive effects of dietary curcumin on the increased activity of renal ornithine decarboxylase in mice treated with a renal carcinogen, ferric nitrilotriacetate," Biochimica et Biophysica Acta, vol. 1740, 2005, pp. 357-366.
Ondrey, "Peroxisome Proliferator-Activated Receptor γ Pathway Targeting in Carcinogenesis: Implications for Chemoprevention," Clinical Cancer Research, vol. 15, No. 1, Jan. 1, 2009, pp. 2-8.
Ongeri et al., "Follicle-Stimulating Hormone Induction of Ovarian Insulin-Like Growth Factor-Binding Protein-3 Transcription Requires a TATA Box-Binding Protein and the Protein Kinase A and Phosphatidylinositol-3 Kinase Pathways," Molecular Endocrinology, vol. 19, No. 7, 2005, pp. 1837-1848.
Osawa et al., "Antioxidative Activity of Tetrahydrocurcuminoids," Bioscience, Biotechnology & Biochemistry, vol. 59, No. 9, 1995, pp. 1609-1612.
Pan et al., "Comparative Studies on the Suppression of Nitric Oxide Synthase by Curcumin and Its Hydrogenated Metabolites through Down-regulation of IκB Kinase and NFκB Activation in Macrophages," Biochemical Pharmacology, vol. 60, 2000, pp. 1665-1676.
Pasqualini et al., "Aminopeptidase N Is a Receptor for Tumor-homing Peptides and a Target for Inhibiting Angiogenesis," Cancer Research, vol. 60, Feb. 1, 2000, pp. 722-727.
Pender et al., "Matrix metalloproteinases and the gut—new roles for old enzymes," Current Opinion in Pharmacology, vol. 4, 2004, pp. 546-550.

(56) References Cited

OTHER PUBLICATIONS

Pendurthi et al., "Suppression of Transcription Factor Egr-1 by Curcumin," Thrombosis Research, vol. 97, 2000, pp. 179-189.
Pereira et al., "Effects of the phytochemicals, curcumin and quercetin, upon azoxymethane-induced colon cancer and 7,12-dimethylbenz[a]anthracene-induced mammary cancer in rats," Carcinogenesis, vol. 17, No. 6, 1996, pp. 1305-1311.
Pfeiffer et al., "Curcuminoids Form Reactive Glucuronides In Vitro," Journal of Agricultural and Food Chemistry, vol. 55, 2007, pp. 538-544.
Plummer et al., "Inhibition of cyclo-oxygenase 2 expression in colon cells by the chemopreventive agent curcumin involves inhibition of NF-κB activation via the NIK/IKK signalling complex," Oncogene, vol. 18, 1999, pp. 6013-6020.
Purkayastha et al., "Curcumin blocks brain tumor formation," Brain Research, vol. 1266, 2009, pp. 130-138.
Rafiee et al., "Effect of curcumin on acidic pH-induced expression of IL-6 and IL-8 in human esophageal epithelial cells (HET-1A): role of PKC, MAPKs, and NF-κB," American Journal of Physiology—Gastrointestinal and Liver Physiology, vol. 296, 2009, G388-G398.
Rao et al., "Chemoprevention of Colon Cancer by Dietary Curcumin," Annals of the New York Academy of Sciences, vol. 768, Sep. 1995, pp. 201-204.
Rasyid et al., "Effect of different curcumin dosages on human gall bladder," Asia Pacific Journal of Clinical Nutrition, vol. 11, No. 4, 2002, pp. 314-318.
Rasyid et al., "The effect of curcumin and placebo on human gall-bladder function: an ultrasound study," Alimentary Pharmacology & Therapeutics, vol. 13, 1999, pp. 245-249.
Roth et al., "Histone Acetyltransferases," Annual Review of Biochemistry, vol. 70, 2001, pp. 81-120.
Saja et al., "Anti-inflammatory effect of curcumin involves downregulation of MMP-9 in blood mononuclear cells," International Immunopharmacology, vol. 7, 2007, pp. 1659-1667.
Sanderson et al., "Dietary Regulation of Intestinal Gene Expression," Annual Review of Nutrition, vol. 20, 2000, pp. 311-338.
Sandur et al., "Curcumin, demethoxycurcumin, bisdemethoxycurcumin, tetrahydrocurcumin and turmerones differentially regulate anti-inflammatory and anti-proliferative responses through a ROS-independent mechanism," Carcinogenesis, vol. 28, No. 8, 2007 pp. 1765-1773.
Sandur et al., "Role of Prooxidants and Antioxidants in the Anti-Inflammatory and Apoptotic Effects of Curcumin (Diferuloylmethane)," Free Radical Biology & Medicine, vol. 43, No. 4, Aug. 15, 2007, pp. 568-580.
Sarraf et al., "Loss-of-Function Mutations in PPARγ Associated with Human Colon Cancer," Molecular Cell, vol. 3, Jun. 1999, pp. 799-804.
Sharma et al., "Pharmacodynamic and Pharmacokinetic Study of Oral Curcuma Extract in Patients with Colorectal Cancer," Clinical Cancer Research, vol. 7, Jul. 2001, pp. 1894-1900.
Sharma et al., "Phase I Clinical Trial of Oral Curcumin: Biomarkers of Systemic Activity and Compliance," Clinical Cancer Research, vol. 10, Oct. 15, 2004, pp. 6847-6854.
Shim et al., "Irreversible Inhibition of CD13/Aminopeptidase N by the Antiangiogenic Agent Curcumin," Chemistry & Biology, vol. 10, Aug. 2003, pp. 695-704.
Shishodia et al., "Curcumin (diferuloylmethane) inhibits constitutive NF-κB activation, induces G1/S arrest, suppresses proliferation, and induces apoptosis in mantle cell lymphoma," Biochemical Pharmacology, vol. 70, 2005, pp. 700-713.
Sindhwani et al., "Curcumin Prevents Intravesical Tumor Implantation of the MBT-2 Tumor Cell Line in C3H Mice," The Journal of Urology, vol. 166, Oct. 2001, pp. 1498-1501.
Singh et al., "Activation of Transcription Factor NF-κB Is Suppressed by Curcumin (Diferulolylmethane)," The Journal of Biological Chemistry, vol. 270, No. 42, Oct. 20, 1995, pp. 24995-25000.
Singh et al., "Mechanism of inhibition of benzo[α]pyrene-induced forestomach cancer in mice by dietary curcumin," Carcinogenesis, vol. 19, No. 8, 1998, pp. 1357-1360.
Sinibaldi et al., "Induction of $p21^{WAF1/CIP1}$ and cyclin D1 expression by the Src oncoprotein in mouse fibroblasts: role of activated STAT3 signaling," Oncogene, vol. 19, 2000, pp. 5419-5427.
Somasundaram et al., "Dietary Curcumin Inhibits Chemotherapy-induced Apoptosis in Models of Human Breast Cancer," Cancer Research, vol. 62, Jul. 1, 2002, pp. 3868-3875.
Song et al., "Curcumin induces human HT-29 colon adenocarcinoma cell apoptosis by activating p53 and regulating apoptosis-related protein expression," Brazilian Journal of Medical and Biological Research, vol. 38, 2005, pp. 1791-1798.
Srinivasan et al., "Protective effect of curcumin on γ-radiation induced DNA damage and lipid peroxidation in cultured human lymphocytes," Mutation Research, vol. 611, 2006, pp. 96-103.
Sugimoto et al., "Curcumin Prevents and Ameliorates Trinitrobenzene Sulfonic Acid—Induced Colitis in Mice," Gastroenterology, vol. 123, 2002, pp. 1912-1922.
Sung et al., "Curcumin circumvents chemoresistance in vitro and potentiates the effect of thalidomide and bortezomib against human multiple myeloma in nude mice model," Molecular Cancer Therapeutics, vol. 8, No. 4, Apr. 2009, pp. 959-970.
Suresh et al., "Tissue distribution & elimination of capsaicin, piperine & curcumin following oral intake in rats," Indian Journal of Medical Research, vol. 131, May 2010, pp. 682-691.
Swamy et al., "Prevention and Treatment of Pancreatic Cancer by Curcumin in Combination With Omega-3 Fatty Acids," Nutrition and Cancer, vol. 60, Supplement No. 1, 2008, pp. 81-89.
Tanaka et al., "Chemoprevention of 4-Nitroquinoline 1-0xide-induced Oral Carcinogenesis by Dietary Curcumin and Hesperidin: Comparison with the Protective Effect of β-Carotene," Cancer Research, vol. 54, Sep. 1, 1994, pp. 4653-4659.
Thaloor et al., "Inhibition of Angiogenic Differentiation of Human Umbilical Vein Endothelial Cells by Curcumin," Cell Growth & Differentiation, vol. 9, Apr. 1998, pp. 305-312.
Thun et al., "Asprin use and Reduced Risk of Fatal Colon Cancer," The New England Journal of Medicine, vol. 325, No. 23, Dec. 5, 1991, pp. 1593-1596.
Tsvetkov et al., "Inhibition of NAD(P)H:quinone oxidoreductase 1 activity and induction of p53 degradation by the natural phenolic compound curcumin,"P Proceedings of the National Academy of Sciences, vol. 102, No. 15, Apr. 12, 2005, pp. 5535-5540.
Usharani et al., "Effect of NCB-02, Atorvastatin and Placebo on Endothelial Function, Oxidative Stress and Inflammatory Markers in Patients with Type 2 Diabetes Mellitus," Drugs in R&D, vol. 9, No. 4, 2008, pp. 243-250.
Vareed et al., "Pharmacokinetics of Curcumin Conjugate Metabolites in Healthy Human Subjects," Cancer Epidemiology, Biomarkers & Prevention, vol. 17, No. 6, Jun. 2008, pp. 1411-1417.
Venkataranganna et al., "NCB-02 (standardized Curcumin preparation) protects dinitrochlorobenzene-induced colitis through downregulation of NFκ-B and iNOS," World Journal of Gastroenterology, vol. 13, No. 7, Feb. 21, 2007, pp. 1103-1107.
Volate et al., "Modulation of aberrant crypt foci and apoptosis by dietary herbal supplements (quercetin, curcumin, silymarin, ginseng and rutin)," Carcinogenesis, vol. 26, No. 8, 2005, pp. 1450-1456.
Wang et al., "Curcumin induces apoptosis through the mitochondria-mediated apoptotic pathway in HT-29 cells," Journal of Zhejiang University—Science B, vol. 10, No. 2, 2009, pp. 93-102.
Weber et al., "TPA-induced up-regulation of activator protein-1 can be inhibited or enhanced by analogs of the natural product curcumin," Biochemical Pharmacology, vol. 72, 2006, pp. 928-940.
Wetzker et al., "Transactivation joins multiple tracks to the ERK/MAPK cascade," Nature Reviews Molecular Cell Biology, vol. 4, Aug. 2003, pp. 651-657.
White et al., "Sodium Butyrate-Mediated Sp3 Acetylation Represses Human Insulin-Like Growth Factor Binding Protein-3 Expression in Intestinal Epithelial Cells," Journal of Pediatric Gastroenterology and Nutrition, vol. 42, Feb. 2006, pp. 134-141.
William et al., "Curcumin inhibits proliferation and induces apoptosis of leukemic cells expressing wild-type or $T_{315}$I-BCR-ABL and

(56) References Cited

OTHER PUBLICATIONS prolongs survival of mice with acute lymphoblastic leukemia," Hematology, vol. 13, No. 6, 2008, pp. 333-343.

Xu et al., "Activation of peroxisome proliferator-activated receptor-γ contributes to the inhibitory effects of curcumin on rat hepatic stellate cell growth," American Journal of Physiology—Gastrointestinal and Liver Physiology, vol. 285, 2003, pp. G20-G30.

Xu et al., "Effects of combined use of curcumin and catechin on cyclooxygenase-2 mRNA expression in dimethylhydrazine-induced rat colon carcinogenesis", J First Mil Med Univ, 2005: 25(1), 5 pages (English language Abstract.

Yallapu et al., "Curcumin nanoformulations: a future nanomedicine for cancer," Drug Discovery Today, vol. 17, Nos. 1-2, Jan. 2012, pp. 71-80.

Yang, "The diverse superfamily of lysine acetyltransferases and their roles in leukemia and other diseases," Nucleic Acids Research, vol. 32, No. 3, 2004, pp. 959-976.

Yodkeeree et al., "Tetrahydrocurcumin inhibits HT1080 cell migration and invasion via downregulation of MMPs and uPA," Acta Pharmacologica Sinica, vol. 29, No. 7, Jul. 2008, pp. 853-860.

Youn et al., "Curcumin ameliorates TNF-α-induced ICAM-1 expression and subsequent THP-1 adhesiveness via the induction of heme oxygenase-1 in the HaCaT cells," Biochemistry and Molecular Biology Reports, vol. 46, No. 8, 2013, pp. 410-415.

Letters from the Editors, Journal of Clinical Psychopharmacology, vol. 28, No. 1, Feb. 2008, pp. 101-122.

Chuah et al., "Enhanced bioavailability and bioefficacy of an amorphous solid dispersion of curcumin", Food Chemistry, 156 (2014), pp. 227-233.

Seo et al., "Preparation and pharmacokinetic evaluation of curcumin solid dispersion using Solutol® HS15 as a carrier", International Journal of Pharmaceutics, 424 (2012), pp. 18-25.

Vasconcelos et al., "Solid dispersions as strategy to improve oral biovailability of poor water soluble drugs", Drug Discovery Today, vol. 12, Nos. 23/24, Dec. 2007.

Wan et al., "Improved Bioavailability of Poorly Water-Soluble Drug Curcumin in Cellulose Acetate Solid Dispersion", AAPS PharmSciTech, vol. 13, No. 1, Mar. 2012, pp. 159-166.

\* cited by examiner

CURCUMINOID COMPLEXES WITH ENHANCED STABILITY, SOLUBILITY AND/OR BIOAVAILABILITY

FIELD OF THE INVENTION

The present invention relates generally to curcumin compositions and/or other curcuminoid compositions useful for the treatment of various diseases including cancer, neurodegeneration, inflammation, and immunodeficiency. In particular, the present invention relates to the material and methods involving curcuminoid formulations, such as curcumin, having a complex formed with a polymethacrylate or methyl methacrylate-based polymer, which has enhanced stability, aqueous solubility and/or bioavailability.

BACKGROUND OF THE INVENTION

For many therapeutic compounds to achieve effective bioavailability and solubility, they must dissolve in gastric fluid and permeate intestinal membranes. The efficacy of therapeutic compounds is generally hindered if they are metabolized too rapidly before, during, or immediately after absorption. For example, the generally low bioavailability of curcumin is attributed to its extremely low aqueous solubility and high rate of metabolism. However, once solublized, curcumin is capable of being effectively absorbed through intestinal membranes and has great potential to prevent and treat a wide spectrum of diseases such as cancer, Alzheimer's disease, inflammatory bowel syndrome, arthritis, etc. Regular consumption of curcumin or curcuminoids has been shown to delay or prevent these diseases. For example, current research has shown that the anti-cancer properties of curcumin may be due to its inhibition of NFKB activation, JNK and AP-1 transcriptional activity. It is well documented that curcumin acts as a potent inhibitor of NFKB signaling pathway which is involved in apoptosis as well as its function has been implicated in inflammation, cell proliferation, differentiation and cell survival. Although curcumin possesses anti-cancer and anti-inflammatory properties, among others, it is still considered extremely safe when administered at very high doses. Conversely, systemic toxicity at high dose rendered other anti-cancer drugs unsuitable for cancer therapy. It was recently reported that uptake of curcumin is safe at doses ranging from 3600-8000 mg/day for four months. In one clinical trial, no toxic effects were seen in patients taking curcumin at a dose of 8 g/day for 18 months.

Despite its therapeutic benefits and non-toxicity at high doses, curcumin has restrictive clinical application because of its extremely low aqueous solubility, rapid systemic metabolism and degradation at alkaline pH, which severely curtails its bioavailability. With respect to solubility, curcumin shows extremely low solubility in aqueous solutions (less than 1 µg/ml in water without any solubility enhancement techniques), but it is soluble in organic solvents such as DMSO, ethanol, methanol, and acetones. Its degradation kinetics have also been reported under various pH conditions, showing relative stability at acidic pHs (i.e., stomach) but unstable at neutral and basic pHs. It has also been reported that most curcumin (>90%) is rapidly degraded within 30 min at pH 7.2 and above. Studies have suggested that this low aqueous solubility, high degradation of curcumin at physiological pHs, and faster metabolism consequently leads to poor absorption, low tissue distribution, and rapid excretion of curcumin that severely restrict its bioavailability. Therefore, a patient must consume large doses of curcumin and curcuminoids in order to achieve detectable serum concentrations needed for its therapeutic benefits. Additionally, the low bioavailability and solubility of curcumin hinders the incorporation of curcumin and curcuminoids into effective pharmaceutical and nutraceutical formulations for both animals and humans.

To address the issues of low aqueous solubility and bioavailability of curcumin, several approaches have been explored, including the use of adjuvants to delay its metabolism and the use of excipients to enhance its bioavailability. However, the adjuvants and excipients thus far identified are not compatible with the use of curcumin and curcuminoids as a regular supplement due to their high costs and lack of practicability. Although adjuvants have been shown to delay or inhibit the metabolism of curcumin and curcuminoids, inhibiting or delaying their metabolism alone without enhancing their solubility will not result in an effective formulation. Therefore, there is a need for a formulation that enhances the bioavailability and solubility of curcumin, such that the therapeutic benefits of this compound can be fully realized.

SUMMARY OF THE INVENTION

The present invention relates generally to curcumin and/or curcuminoid formulations useful for the treatment of various diseases including cancer, neurodegeneration, inflammation, and immunodeficiency. Specifically, the present invention provides a composition comprising nanoparticles/microparticles loaded with one or more curcuminoid-eudragit complexes, the one more curcuminoid-eudragit complexes presenting enhanced stability, aqueous solubility and/or bioavailability of the curcuminoid component.

In some aspects, the curcuminoid component is chosen from curcumin, demethoxycurcumin, bisdemethoxycurcumin, tetrahydroxycurcumin, Bis-0-Demethyl curcumin (BDMC), or combinations thereof.

In some aspects, the eudragit component comprises a polymer or co-polymer having a backbone comprising polymethacrylate or methyl methacrylate, such that the eudragit component may have various different functional side-chains attached thereto.

In some aspects of the present invention, a medicament preparation comprises a curcuminoid component and a eudragit component, the curcuminoid component chosen from curcumin, demethoxycurcumin, bisdemethoxycurcumin, tetrahydroxycurcumin, Bis-0-Demethyl curcumin (BDMC), or combinations thereof, wherein at least a portion of the curcuminoid component and at least a portion of the eudragit component are in the form of a curcuminoid-eudragit complex.

In some aspects of the present invention, the eudragit has a backbone of a polymethacrylate-based copolymer or methyl methacrylate-based copolymer. In some aspects, the polymethacrylate-based copolymer is anionic, cationic or a neutral copolymer.

In some aspects of the present invention, the medicament preparation further comprises an adjuvant. In some aspects, the adjuvant is a P-glycoprotein inhibitor or an inhibitor of glucouronidation. In some aspects, the adjuvant is piperine.

In some aspects of the present invention, the curcuminoid component of the medicament preparation has a solubility in water in an amount greater than 1 µg/ml, in some aspects greater than 5 µg/ml, in some aspects greater than 10 µg/ml, in some aspects greater than 20 µg/ml, in some aspects greater than 30 µg/ml, in some aspects greater than 40 µg/ml, in some aspects greater than 50 µg/ml, in some aspects greater than 75 µg/ml, in some aspects greater than 100 µg/ml, in some aspects greater than 200 µg/ml, in some aspects greater than 300 µg/ml, in some aspects greater than 400 µg/ml, in some aspects greater than 500 µg/ml, in some aspects greater than 600 µg/ml, in some aspects greater than 700 µg/ml, in some aspects greater than 800 µg/ml, in some aspects greater than 900 µg/ml, in some aspects greater than 1 mg/ml, in some aspects greater than 5 mg/ml, in some aspects greater than 10 mg/ml, in some aspects greater than 15 mg/ml, in some aspects greater than 20 mg/ml, and in some aspects greater than 50 mg/ml.

In some aspects, the aqueous solubility of the curcuminoid component of the medicament preparation is between about 1 µg/ml and about 50 mg/ml, in some aspects between about 10 µg/ml and about 40 mg/ml, in some aspects between about 100 µg/ml and about 20 mg/ml, and in some aspects between about 1 mg/ml and about 20 mg/ml.

In some aspects, the aqueous solubility of the curcuminoid component of the medicament preparation is between about 1 mg/ml and about 50 mg/ml, in some aspects between about 10 mg/ml and about 25 mg/ml, in some aspects between about 10 µg/ml and about 50 mg/ml, and in some aspects between about 25 mg/ml and about 50 mg/ml.

In some aspects of the present invention, the medicament preparation can further comprise an ampiphatic component or surfactant that facilitates the formation of curcumin-eudragit nanoparticles or microparticles. In some aspects, the surfactant is (e.g., polyvinyl alcohol or PVA), which can enhance the loading of curcumin as well as aid in the solubilization process.

In other aspects, the medicament preparation further comprises other adjuvants, excipients, nutraceuticals, and/or pharmaceuticals providing additional therapeutic benefits.

In some aspects of the present invention, the medicament preparation is in the form of a solid (e.g., tablet or pill), a liquid (e.g., solution, suspension or lotion), or semisolid (e.g., gel, cream or ointment). In other embodiments, the composition of curcumin-eudragit complexes can be injected into the patient's body. In still other embodiments, the composition of curcumin-eudragit complexes can be applied topically to the patient's skin, or inserted into a patient's bodily orifice such as intranasally, through pulmonary administration, rectally or vaginally.

In some aspects of the present invention, a curcumin formulation with enhanced bioavailability comprises a complex comprising a curcumin and/or a curcuminoid component and a polymer or copolymer component, the polymer or copolymer compoing having a backbone comprising polymethacrylate or methyl methacrylate. In some aspects, the polymer or copolymer is a polymethacrylate-based copolymer, and further includes anionic, cationic, and neutral copolymers (e.g., Eudragit® EPO or Eudragit® S-100) that enhances the solubilization of curcumin. In other aspects, the curcumin used in the formulation can exist as -keto or -enol forms, or the curcumin used can be a combination of different commercially available forms of curcumin. In some aspects, the curcuminoid comprises curcumin, demethoxycurcumin, bisdemethoxycurcumin, tetrahydroxycurcumin, Bis-0-Demethyl curcumin (BDMC), or combinations thereof. In some aspects, the polymer or copolymer and the curcumin used in the formulation can form a complex based on intermolecular interactions (e.g., hydrophobic interactions or hydrogen bonding), which enhances the aqueous solubility, stability and/or the bioavailability of the curcumin and/or curcuminoid component. In some aspects, the polymer or copolymer and the curcuminoid used in the formulation can form a complex based on intermolecular interactions (e.g., hydrophobic interactions or hydrogen bonding), which enhances the aqueous solubility, stability and/or the bioavailability of the curcumin and/or curcuminoid component.

In some aspects of the present invention, the formulation further comprises an adjuvant that delays or inhibits curcumin metabolism. In some aspects, the adjuvant is a P-glycoprotein inhibitor or an inhibitor of glucouronidation. In some aspects, the adjuvant can be piperine. Delaying the metabolism of curcumin using piperine enhances its therapeutic effects by enabling it to persist longer in the patient and provides more time for penetration into target tissues.

In some aspects, the present invention features a method of forming a medicament preparation comprising particulate formulations (i.e., nanoparticles/microparticles) loaded with curcumin-eudragit complexes having enhanced stability, aqueous solubility and/or bioavailability using sonication and precipitation techniques.

In some aspects, curcumin and/or other curcuminoids and a eudragit can be dissolved and then added to an aqueous solution containing a surfactant. In some cases, this process can be performed using sonication or precipitation techniques. The resulting nanoparticles or microparticles can be collected and analyzed for the amount of curcumin accumulation present in the particles. In some cases, different formulation and process parameters (e.g., type and concentration of organic solvent or surfactant used, curcumin to eudragit polymer ratio, etc.) can be used in order to alter the formulation to obtain increased or decreased loading and/or increased or decreased solubility. For example, in some cases, the particle size can be altered by changing the surfactant type (e.g., Tween-20, Pluronic F68, or polyvinyl alcohol) and the surfactant concentration (1%, 2%, or 3% w/v) in the preparation. The amount of curcumin and/or other curcuminoid accumulation present in the particles can be enhanced by changing the ratio between the curcumin and/or other curcuminoid with the eudragit polymer (e.g., 1:5, 1:3, or 1:2). Other parameters can also be altered to change the size of the particles, including the amount of energy used during sonication and total sonication time.

In some aspects, the curcuminoid component and the eudragit component can form a curcuminoid-eudragit complex by melting the curcuminoid component and the eudragit component.

In some aspects of the present invention, a method of treating patients for diseases involving cancer, neurodegeneration, inflammation, and immunodeficiency comprises administering a medicament preparation comprising nanoparticles loaded with curcumin-eudragit complexes, the medicament preparation having enhanced bioavailability of the curcumin component. The curcumin-eudragit complexes of the present invention can enhance the bioavailability of curcumin up to or more than 20,000 times compared to free curcumin.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the present invention will be apparent from the following detailed description, and from the claims.

BRIEF DESCRIPTION OF THE DRAWINGS

The present invention can be more completely understood in consideration of the following detailed description of various embodiments of the present invention in connection with the accompanying drawings, in which.

DETAILED DESCRIPTION OF THE INVENTION

Figure 1:
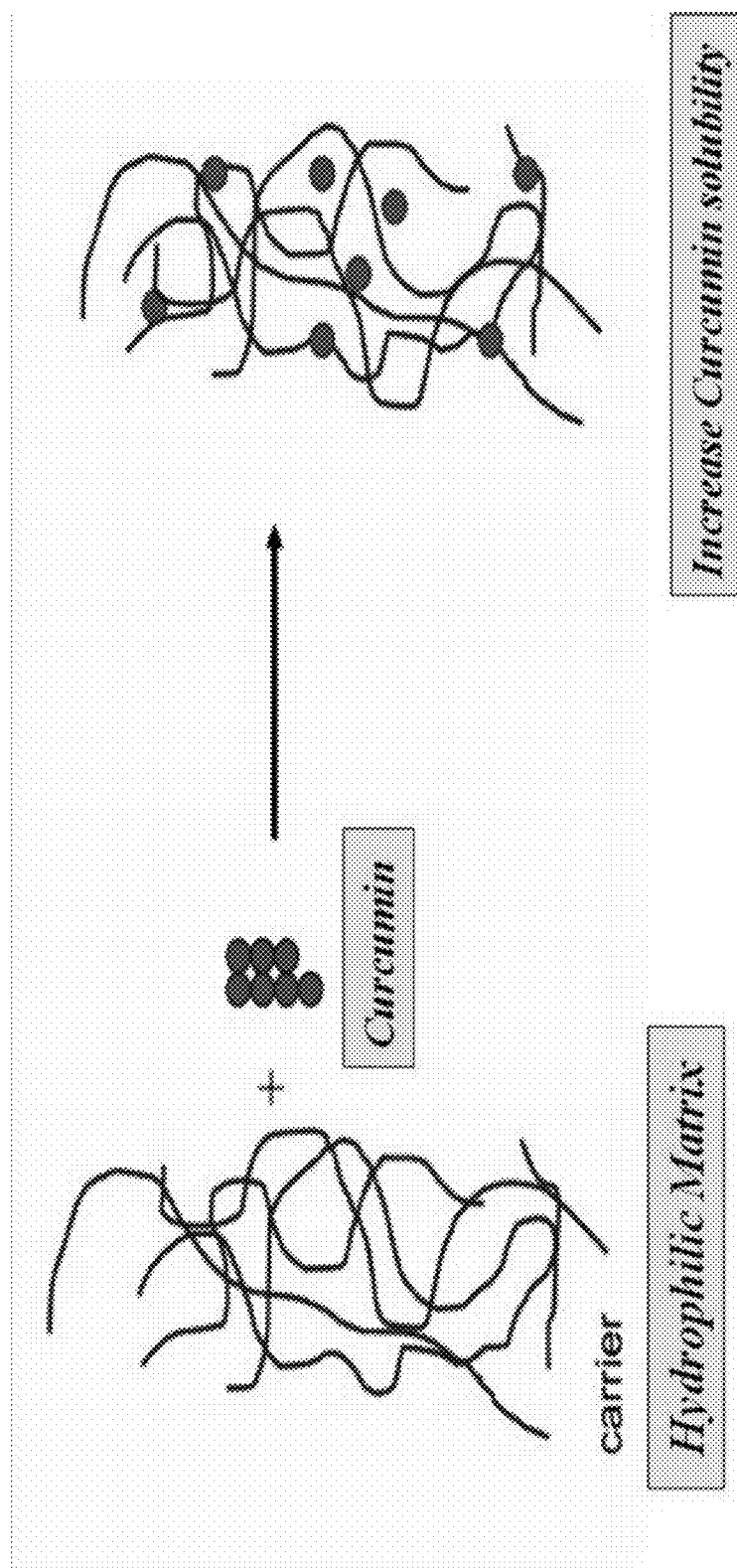
FIG. 1 is an illustration of the molecular complex formed between curcumin and a eudragit polymer in order to increase the stability, aqueous solubility and/or bioavailability of curcumin, according to certain aspects of the present invention. This illustration is also representative of other curcuminoids alone or in combination of curcumin that can form a complex with a eudragit polymer according to certain other aspects of the present invention.

Embodiments of the present invention are discussed in detail below. In describing embodiments, specific terminology is employed for the sake of clarity. However, the present invention is not intended to be limited to the specific terminology so selected. A person skilled in the relevant art will recognize that other equivalent parts can be employed and other methods developed without parting from the spirit and scope of the present invention. All references cited herein are incorporated by reference as if each had been individually incorporated.

"Treat" refers to preventing, curing, reversing, attenuating, alleviating, minimizing, suppressing or halting at least one of the symptoms or deleterious effects of the diseases, disorders or conditions described herein. Treatment encompasses both therapeutic treatment and prophylactic or preventative measures. Those in need of treatment include those already with the disorder as well as those in which the disorder is to be prevented. Hence, the patient to be treated may have been diagnosed as having the disorder or may be predisposed or susceptible to the disorder.

"Effective" or "therapeutically effective" means sufficient to cause at least one of a patient's symptoms to decrease in frequency and/or intensity. The symptoms that are decreased in frequency and/or intensity can include, for example, one or more adverse cognitive or physiological symptoms.

"Administer" means to deliver one or more doses of one of the compositions to a patient. The methods of the present inventions can involve administration of the composition by any means and via any route of administration that is consistent with effective treatment of one or more of the diseases described herein. For example, the methods can involve administering the compositions orally, topically on the skin, intranasally and/or using injections.

The "patient" according to the present invention is a mammal, such as a human, which is diagnosed with one of the diseases, disorders or conditions described herein, or is predisposed to at least one type of the diseases, disorders or conditions described herein. The compositions of the present invention can be administered to any mammal that can experience the beneficial effects of the compositions and methods of the invention. Any such mammal is considered a "patient." Such patients include humans and non-humans, such as humans, domestic and farm animals, and zoo, sports, or pet animals, such as dogs, horses, cats, cows, mice, rats, etc.

The term "curcumin" herein mentioned refers to the principal curcuminoid of turmeric. As described herein, curcumin can be used alone or in combination with other curcuminoids (e.g., demethoxycurcumin or bisdemethoxycurcumin).

The term "curcuminoid(s)" herein mentioned refers to a derivative of curcumin (e.g., demethoxycurcumin, bisdemethoxycurcumin, tetrahydroxycurcumin, Bis-0-Demethyl curcumin (BDMC), or combinations thereof), and/or derivatives of one or more of curcumin, demethoxycurcumin, bisdemethoxycurcumin, tetrahydroxycurcumin or Bis-0-Demethyl curcumin (BDMC).

The term "eudragit" herein mentioned refers to a polymer or co-polymer having a backbone containing polymethacrylate or methyl methacrylate-based polymer, with such polymer or co-polymer capable of having various different functional side-chains attached to such backbone.

The term "surfactant" herein mentioned refers to an amphipathic molecule, including such molecules that are anionic, cationic, nonionic, synthetic or natural.

Figure 8:
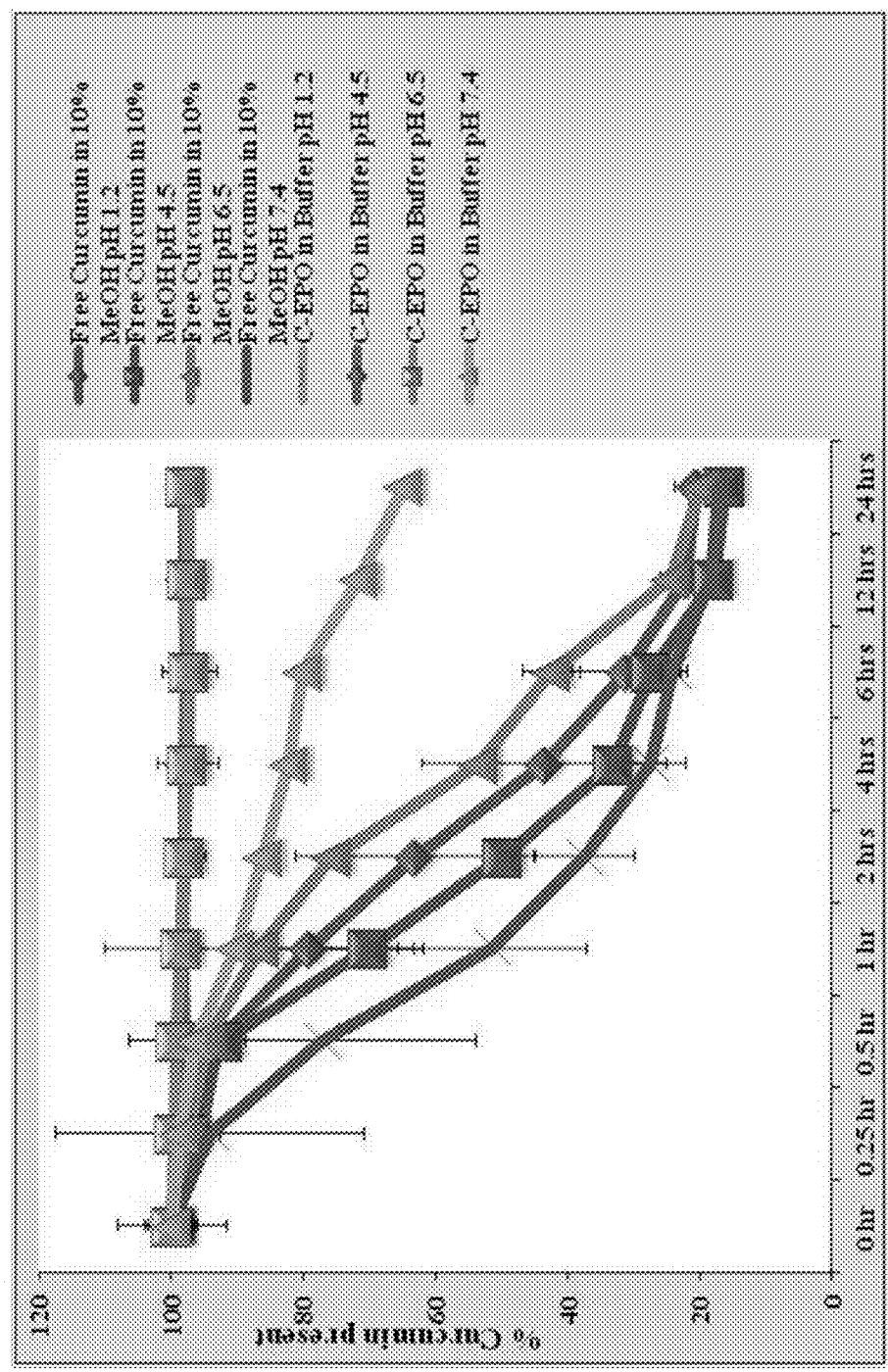
FIG. 8 presents a graph of the stability of aqueously soluble curcumin-eudragit complexes at pH 1.2, 4.5, 6.8, or 7.4, according to certain aspects of the present invention, with free curcumin or the equivalent amount of curcumin-Eudragit® EPO complexes solubilized in 10% methanol in each respective buffer and incubated at 37 C. At different time points, the samples were centrifuged (20,000 g), and the supernatant was passed through 0.2 µm filter, and the amount of soluble and stable curcumin in the filtrate was determined by UV absorbance at 420 nm.

The present invention relates generally to curcumin and/or curcuminoid formulations useful for the treatment of diseases involving cancer, neurodegeneration, inflammation, and immunodeficiency. Specifically, in some aspects, the present invention provides a composition comprising nanoparticles or microparticles loaded with curcumin-eudragit complexes having enhanced stability, aqueous solubility and/or bioavailability. As shown in FIG. 8, the presence of a eudragit enhances the stability of aqueous soluble curcumin-eudragit complexes over a broad pH range, such as pH of 1.2, 4.5, 6.8, 7.4 or higher, compared to free curcumin dissolved in 10% methanol.

In some aspects of the present invention, a method of treating patients for diseases involving cancer, neurodegeneration, inflammation, and immunodeficiency comprises administering a medicament preparation comprising nanoparticles loaded with curcumin-eudragit complexes, the medicament preparation having enhanced bioavailability of the curcumin component.

Curcumin is the active curcuminoid of turmeric and also known as C.I. 75300, diferuloylmethane, or Natural Yellow 3. The systematic chemical name of curcumin is (1E,6E)-1,7-bis(4-hydroxy-3-methoxyphenyl)-1,6-heptadiene-3,5-dione. Curcumin has the following chemical structure:

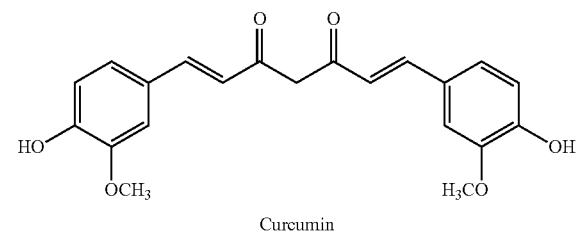 [SMILES: COc1cc(/C=C/C(=O)CC(=O)/C=C/c2ccc(O)c(OC)c2)ccc1O]

Curcumin

Curcumin can exist at least in two tautomeric forms, keto and enol. The -keto form is preferred in solid phase and the -enol form in solution. For example, in acidic solutions (e.g., pH<7.4) curcumin turns yellow, whereas in basic solutions (e.g., pH>8.6), curcumin turns bright red. The biological effects of curcumin involve the inhibition of metabolic enzymes, which can result in antioxidant, anti-inflammatory, and anti-tumor activity. Commercially available curcumin can comprise approximately 77% diferuloylmethane (curcumin), 17% demethoxycurcumin, and 6% bisdemethoxycurcumin. In some cases, curcuminoids (i.e., derivatives of curcumin) can be synthesized to enhance the solubility of curcumin and hence, its bioavailability. For example, other curcuminoids besides curcumin include demethoxycurcumin, bisdemethoxycurcumin, tetrahydroxycurcumin, and Bis-0-Demethyl curcumin (BDMC). In some cases, curcuminoids or other curcumin derivatives can be used independently or in combination to enhance stability, aqueous solubility, bioavailability and/or therapeutic efficacy. As examples of other curcuminoids, the curuminoids demethoxycurcumin and bisdemethoxycurcumin have the following chemical structures:

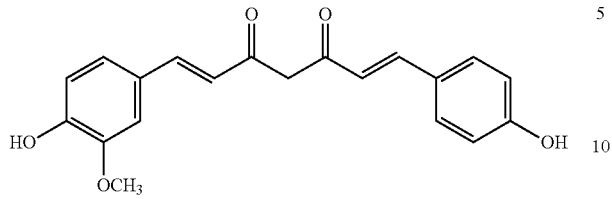

Demethoxycurcurmin

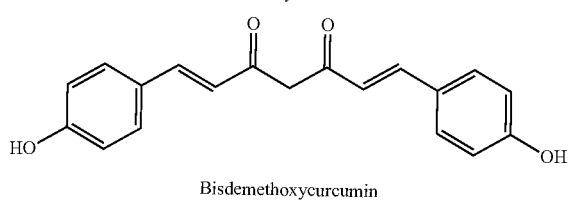

Bisdemethoxycurcumin

As illustrated in FIG. 1, curcumin can be combined with a eudragit, which provides a hydrophilic matrix, to form a curcumin-eudragit complex that increases the aqueous solubility of curcumin, and in turn, its stability and/or bioavailability. While FIG. 1 illustrates curcumin, the figure is equally representative of other curcuminoids alone or in combination with curcumin that can be combined with a eudragit to form a complex that increases the solubility of the curcumin and/or curcuminoids, and in turn, its stability, aqueous solubility and/or bioavailability.

Eudragits copolymers are derived from esters of acrylic and methacrylic acid. In some aspects, eudragit polymers that form a complex with curcumin and/or other curcuminoids according to certain aspects of the present invention comprise a polyacrylate or polymethylacrylate backbone in addition to functional groups which provide unique physiochemical properties (e.g., solubility at different pHs). In some aspects, a eudragit comprising a polyacrylate or polymethacrylate backbone and an anionic, cationic, or neutral functional group/copolymer can enhance the stability, aqueous solubility and/or bioavailability of curcumin and/or other curcuminoids.

For example, the eudragit copolymer can comprise Eudragit® EPO, available from Evonik Industries, which is a cationic copolymer based on dimethylaminoethyl methacrylate, butyl methacrylate, and methyl methacrylate. In some other aspects, the eudragit copolymer can comprise Eudragit® S-100, available from Evonik Industries, which is an anionic copolymer based on methacrylic acid and methyl methacrylate. The eudragit copolymers Eudragit® EPO and Eudragit® S-100 have the following chemical structures:

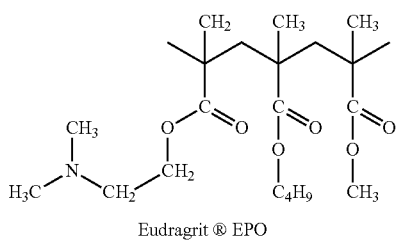

Eudragrit ® EPO

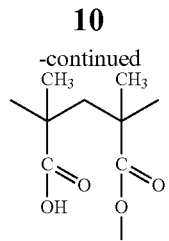

Eudragrit ® S-100

For example, the curcumin formulation of the present invention can include Eudragit EPO® comprising pH-dependent cationic copolymers soluble in gastric fluid or tissues (e.g., stomach) up to a pH of about 5.0. Additionally, for example, the curcumin formulation of the present invention can include Eudragit S100® comprising pH-dependent anionic copolymers soluble in intestinal fluid or tissues (e.g., ileum and colon) ranging between approximately pH 6.5 to approximately 7.5. In still other aspects, the curcumin formulation of the present invention can include curcumin-eudragit complexes having various eudragits, such that the curcumin formulation has additional or synergistic benefits. One of ordinary skill in the art shall appreciate that other eudragits can be chosen depending on the pH of the specific tissue or tissues targeted for curcumin and/or other curcuminoid therapy.

For example, the combination of and curcumin Eudragit® S100 may be more beneficial for inflammatory bowel disease, such that the Eudragit® EPO will dissolve in the stomach and curcumin will be absorbed and will be delivered to the target colon tissue through blood supply. However, Curcumin-Eudragit® S100 complexes will not dissolve in any part of the intestine until such complexes reach the colon (pH~7.0) and deliver curcumin locally at the colon site through lumen. Thus, by delivering curcumin both systemically through blood supply and locally at the lumen will be more beneficial to the respective patient.

In some embodiments, the eudragit can be chosen from the class of eudragit copolymers Eudragit® E, available from Evonik Industries, which are a cationic copolymer based on dimethylaminoethyl methacrylate, butyl methacrylate and methyl methacrylate having a pendant tertiary amine group, which can enhance curcumin aqueous solubility at a pH up to above 5.0 (i.e., the stomach).

In some other embodiments, the eudragit can be chosen from the class eudragit copolymers Eudragit® S, also available from Evonik Industries, which are anionic copolymers based on methacrylic acid and methyl methacrylate having a carboxylic acid group, which can enhance curcumin aqueous solubility at pH of about 7.0 and above (i.e., lower intestine).

In some other embodiments, it is contemplated that the eudragit can be chosen from the class eudragit copolymers Eudragit® L, also available from Evonik Industries, which contain an anionic copolymers based on methacrylic acid and ethyl acrylate, which can enhance curcumin aqueous solubility.

In some other embodiments, it is contemplated that the eudragit may be chosen from the class eudragit copolymers Eudragit® R, also available from Evonik Industries, is a copolymer of ethyl acrylate, methyl methacrylate and a low content of methacrylic acid ester with quaternary ammonium groups. These eudragits are time controlled, pH independent. Examples include Eudragit® RL 100, Eudragit®

RL PO, Eudragit® RL 30 D, Eudragit® RL 12,5, Eudragit® RS 100, Eudragit® RS PO, Eudragit® RS 30 D, and Eudragit® RS 12,5.

In some other embodiments, it is contemplated that the eudragit can be chosen from the class eudragit copolymers Eudragit® N, also available from Evonik Industries, which is a neutral copolymer based on ethyl acrylate and methyl methacrylate. These eudragits are time controlled, pH independent. Examples include Eudragit® NE 30 D, Eudragit® NE 40 D and Eudragit®NM 30 D.

The foregoing examples provide a non-exhaustive list of eudragits that are contemplated to form complexes with curcumin and/or other curcuminoids according to certain aspects of the present invention. A representative list of eudragits that can form a complex with curcumin and/or other curcuminoid with potential target tissue dissolution and the corresponding pH is provided in Table 1.

TABLE 1

Examples of eudragits and their corresponding approximate pH ranges, target tissues, and chemical structure.

| Eudragit | Approximate pH | Target Tissue |
| --- | --- | --- |
| Eudragit ® E 100 | 1-5 | Stomach |
| Eudragit ® E 12.5 | 1-5 | Stomach |
| Eudragit ® EPO | 1-5 | Stomach |
| Eudragit ® L-30 D-55 | >5.5 | Duodenum |
| Eudragit ® L 100-55 | >5.5 | Duodenum |
| Eudragit ® L 100 | 6-7 | Jejunum |
| Eudragit ® L 12.5 | 6-7 | Jejunum |
| Eudragit ® S 100 | >7.0 | Ileum, Colon |
| Eudragit ® S 12.5 | >7.0 | Ileum, Colon |
| Eudragit ® FS 30 D | >7.0 | Ileum, Colon |
| Eudragit ® RL 100 | Independent - time released | |

Figure 2:
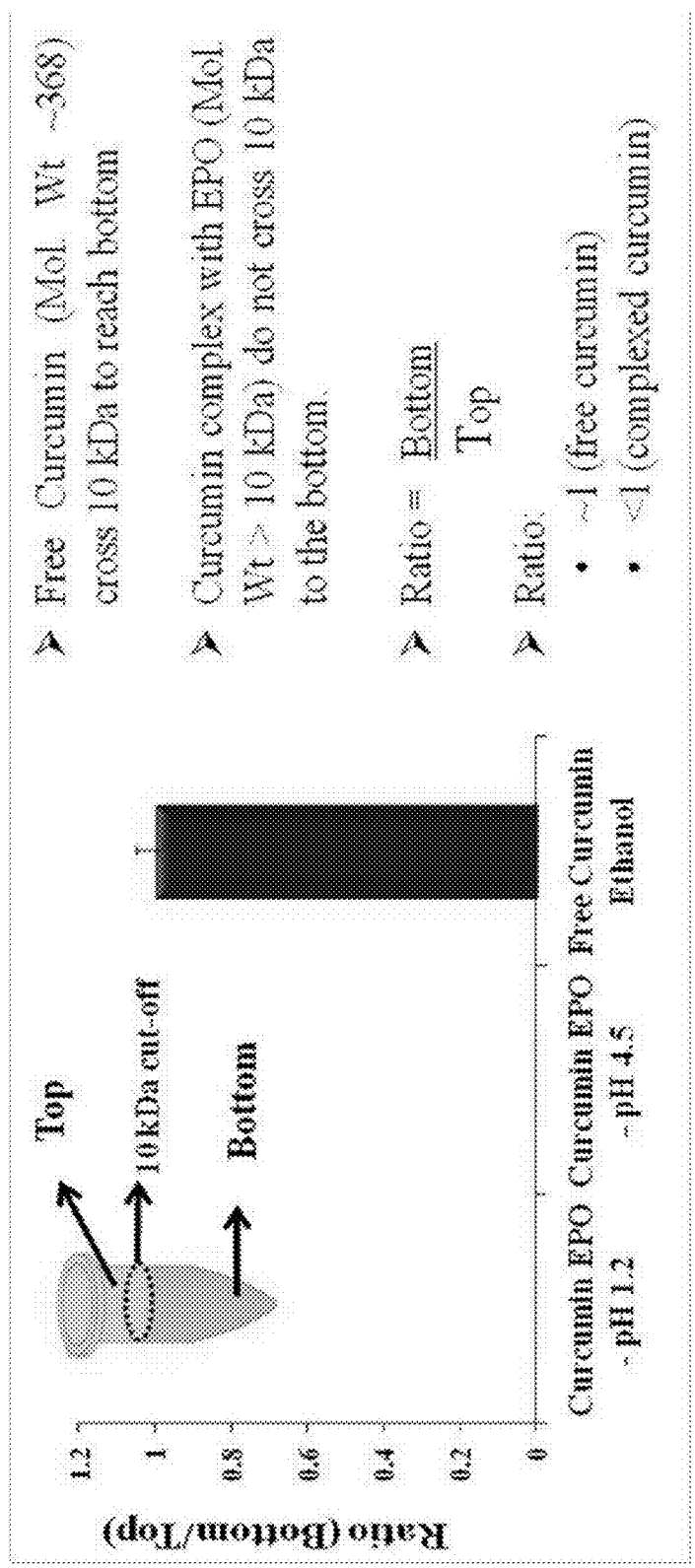
FIG. 2 presents a graph relating to a sample of (i) free curcumin dissolved in ethanol, and (ii) samples of the complex formed between curcumin and Eudragit® EPO dissolved in an aqueous solution at pH 1.2 and 4.5, respectively, according to certain aspects of the present invention. The free curcumin and curcumin-Eudragit® EPO complexes having been passed through a 10 KDa molecular weight cut-off membrane, such that curcumin that is smaller and Eudragits that are higher than 10 KDa in their molecular weight, resulted in free curcumin passing freely through the membrane unless it formed a complex with the high molecular weight eudragit, such as in the complex samples illustrated. The ratio of the concentration of dissolved curcumin before and after filtration was determined by UV-spectrophotometry and plotted on the Y-axis. As shown in the present graph, a ratio of about 1 indicates no complex formation, such as in the free curcumin dissolved in ethanol, while a ratio less than 1 indicates complex formation between curcumin and Eudragit® EPO.

In some aspects, a eudragit can form a complex with curcumin and/or one or more curcuminoids based on intermolecular interactions (e.g., hydrophobic interactions or hydrogen bonding), which enhances the bioavailability of curcumin and/or the one or more curcuminoids. As illustrated in FIG. 2, in one embodiment of the present invention, Eudragit EPO® forms a complex with curcumin at pH 1.2 and 4.5, which prevents it from crossing the 10 kDa filter. As also shown in FIG. 2, in the absence of the eudragit, free curcumin passes through the 10 kDa filter and precipitates. According to some aspects, the methacrylic acid backbone of some eudragits can be the basis of the intermolecular interaction with curcumin, in which case, the interaction would be independent of the cationic or anionic copolymer of the eudragit. In other aspects, the basis of the complex formation can be an ionic interaction involving the cationic or anionic copolymers.

Figure 6A:
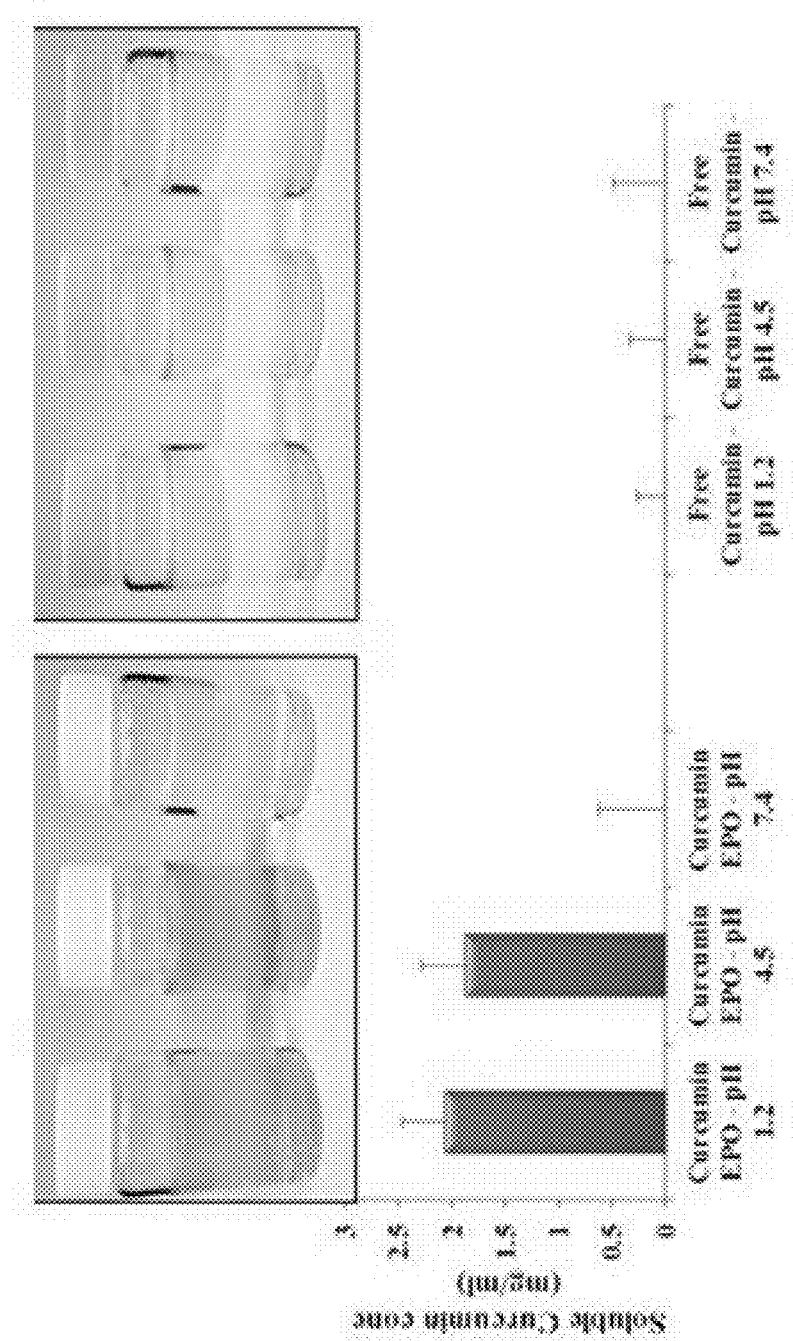
FIG. 6A presents a graph with corresponding images of aqueous solubility of curcumin measured in mg/ml at pH 1.2, 4.5, and 7.4, according to certain aspects of the present invention, with a solution with a yellow color indicating fully dissolved curcumin (i.e., left panel, first and second solutions), while a clear solution indicating absence of soluble curcumin (i.e., left panel, third solution; right panel, first, second, and third solutions). The concentration of dissolved curcumin in water in the shown bottles being represented in the corresponding bar graph below. The left panel represents Curcumin-eudragit-EPO complexes and the right panel represents free uncomplexed curcumin.
Figure 6B:
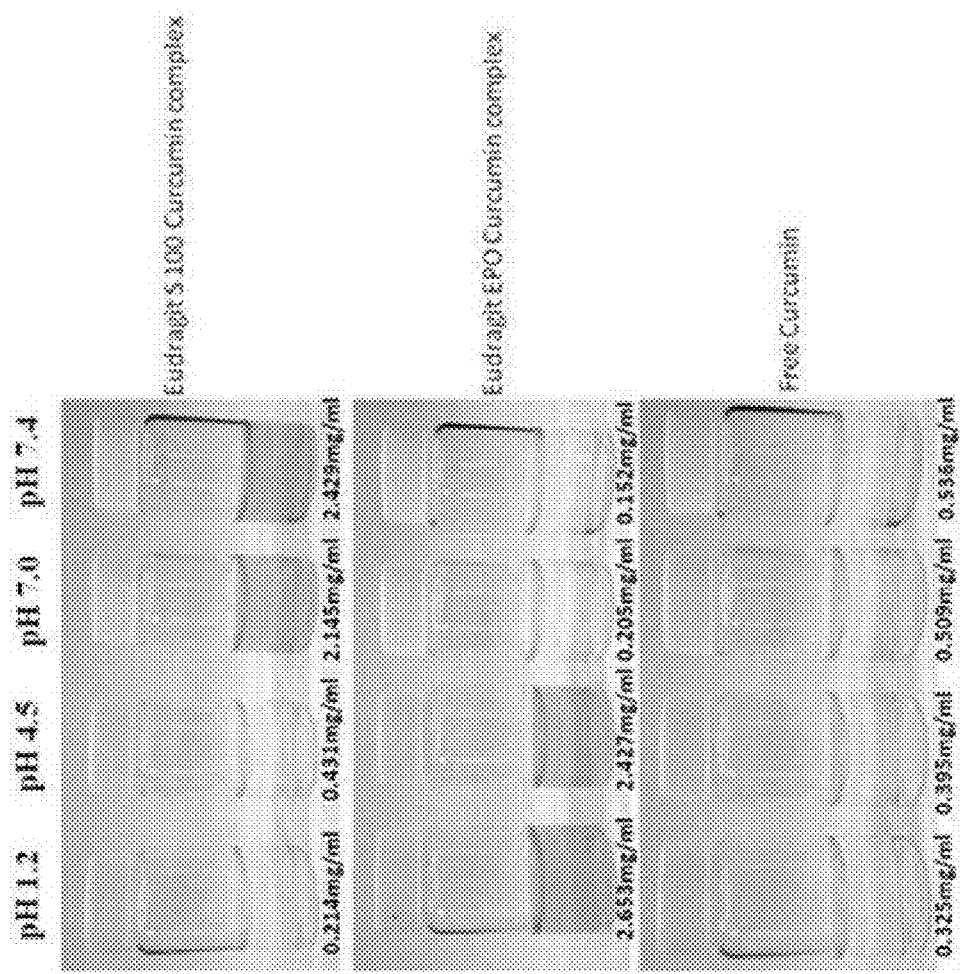
FIG. 6B illustrates that aqueous soluble curcumin-eudragit complexes can be made with other eudragits other than Eudragit® EPO. Curcumin complexes were made with both Eudragit® EPO and Eudragit® S100. The aqueous solubility of these complexes depends on the chemical groups on the side chain of the eudragits and the pH of the aqueous solution. Images of curcumin solubility measured in mg/ml at pH 1.2, 4.5, 7.0, and 7.4, according to certain aspects of the present invention, with a solution with a yellow color indicates fully dissolved curcumin (i.e., top panel of Eudragit® 5100, third and fourth solutions; middle panel of Eudragit® EPO, first and second solutions), while a clear solution indicates absence of soluble curcumin (i.e., top panel of Eudragit® 5100, first and second solutions; middle panel Eudragit® EPO, third and fourth solutions; bottom panel of free curcumin, first, second, third, and fourth solutions).

In some aspects, the formation of curcumin-eudragit complexes with enhanced bioavailability according to certain embodiments of the present invention involves the use of solubilization and precipitation techniques. As shown in FIGS. 6A and 6B, curcumin solubility is enhanced due to the presence of a eudragit. For example, as shown in FIGS. 6A and 6B, curcumin solubility is enhanced at pH of about 1.2 and pH of about 4.5 (i.e., yellow color) when complexed with Eudragit® EPO as compared to free curcumin. Additionally, as shown in FIG. 6B, curcumin solubility can also be enhanced at pH 7.0 and pH 7.4 when complexed with Eudragit® S100 (top panel) as compared to free curcumin. Depending on the eudragit used to form the complex with curcumin and/or curcuminoids, fluids or tissues with different pHs can be differentially targeted for curcumin therapy. For example, Eudragit S100® can be used to deliver curcumin to the ileum and colon, while Eudragit® EPO can be used to deliver curcumin to the stomach.

Figure 3:
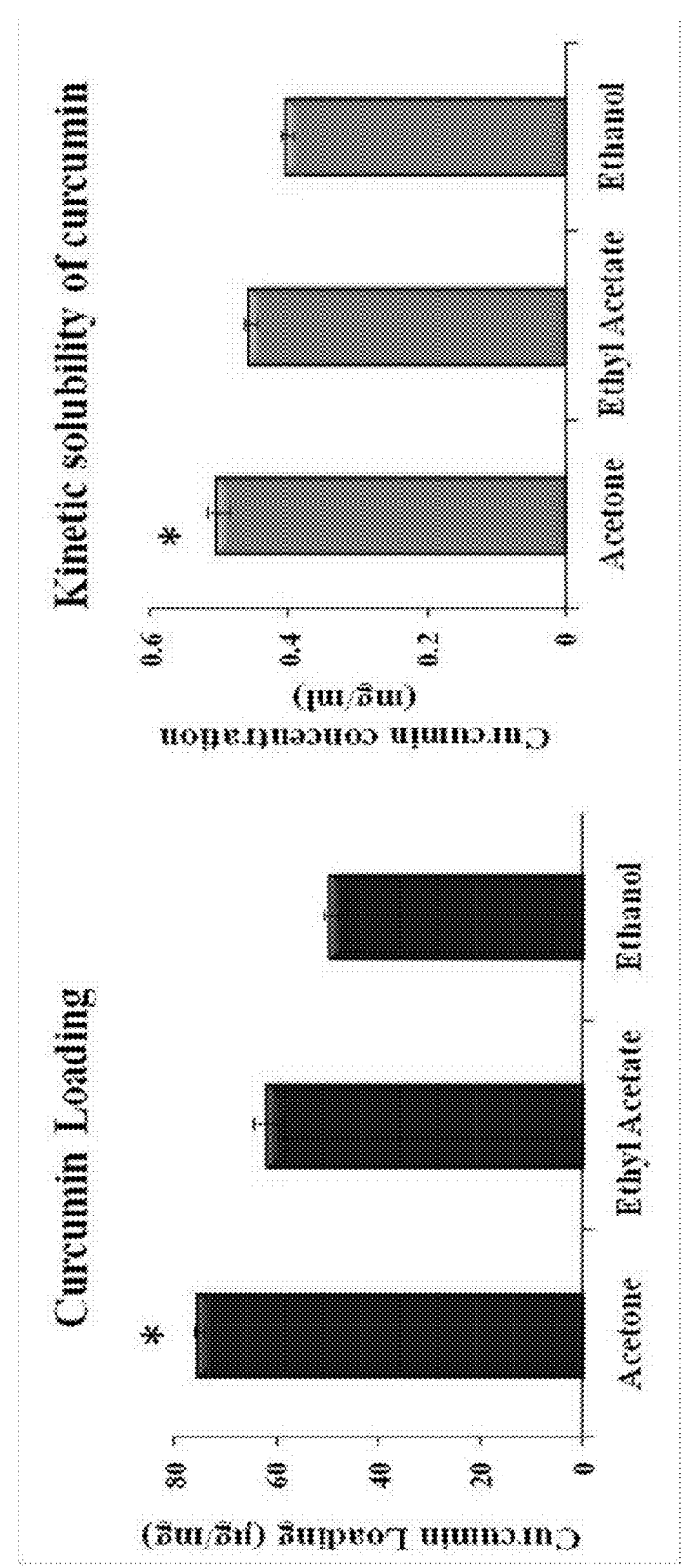
FIG. 3 presents a set of graphs relating to the effects of organic solvents on the formation of the curcumin-eudragit complexes, according to certain aspects of the present invention, with the eudragit comprising Eudragit® EPO, and the data represent mean±standard deviation. Loading represents µg of curcumin present in 1 mg of the formulation, and the "*" indicates statistical significance (P<0.05) as compared to the ethyl acetate group.
Figure 4:
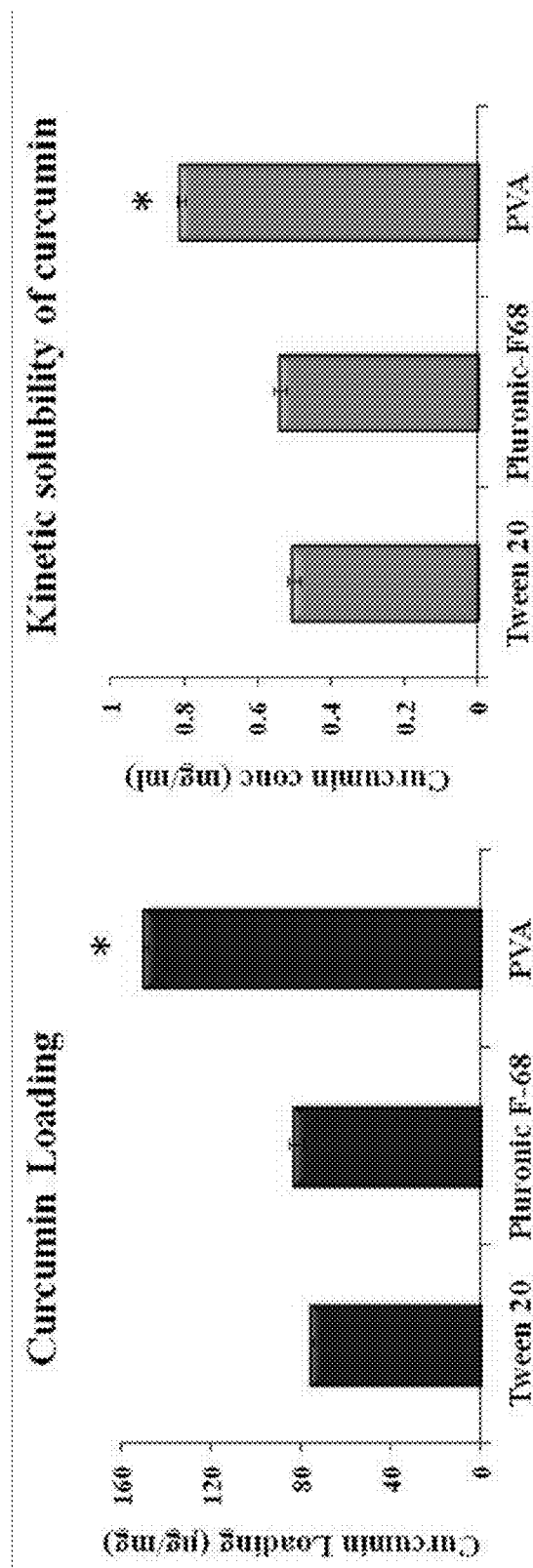
FIG. 4 presents a set of graphs relating to effects of surfactants on the formation of the curcumin-eudragit complexes, according to certain aspects of the present invention, with the eudragit comprising Eudragit® EPO, and the data represent mean±standard deviation. Loading represents µg of curcumin present in 1 mg of the formulation, and the "*" indicates statistical significance (P<0.05) as compared to pluronuc F-68.
Figure 5:
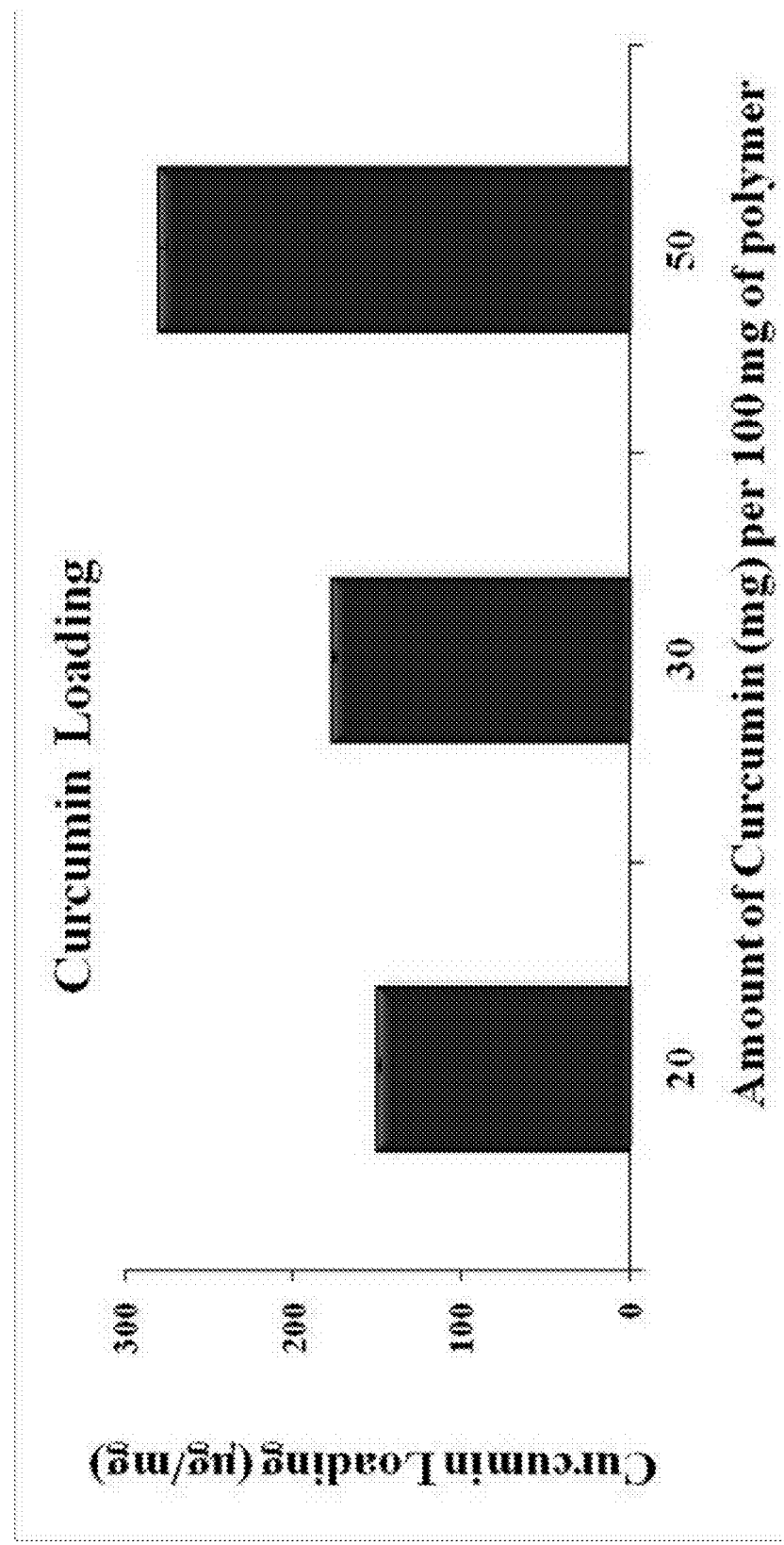
FIG. 5 presents a graph relating to the different amounts of curcumin (mg) that may be used to form a complex with the eudragit polymer, according to certain aspects of the present invention, with the eudragit comprising Eudragit® EPO, and the data represent mean±standard deviation. Loading represents µg of curcumin present in 1 mg of the formulation, with up to 50 mg of curcumin being capable of being added per 100 mg of the eudragit polymer, according to certain aspects of the present invention.

In some aspects, curcumin and a eudragit can be dissolved and then added to an aqueous solution containing a surfactant, such as shown in FIGS. 3 and 4. In some cases, this process can be performed under other co-precipitation techniques. The resulting particle complexes can be collected and analyzed for the amount of curcumin present in the particles. As shown in FIG. 5, at least 50 mg of curcumin can be added per 100 mg of the eudragit polymer. In some cases, different formulation and process parameters (e.g., type and concentration of organic solvent or surfactant used, curcumin to eudragit polymer ratio, etc.) can be used in order to alter the formulation to obtain increased or decreased loading and/or increased or decreased solubility.

As shown in FIG. 3, the use of different organic solvents alter the solubility of the curcumin-eudragit complexes. In some cases, as shown in FIG. 4, the particle size can be altered by changing the surfactant type (e.g., Tween-20, Pluronic F68, or polyvinyl alcohol) and the surfactant concentration in the preparation. In some embodiments, the surfactant concentration is between 1% and 20% w/v. In some embodiments, the surfactant concentration is between 1% and 3% w/v. In some embodiments, the surfactant concentration is between 1% and 5% w/v. In some embodiments, the surfactant concentration is between 3% and 5% w/v. In some embodiments, the surfactant concentration is between 5% and 10% w/v. In some embodiments, the surfactant concentration is 1%, 2%, 3%, 4%, 5%, 6%, 7%, 8%, 9%, 10%, 15%, or 20% w/v.

The amount of curcumin accumulation present in the particles can be enhanced by changing the curcumin (and/or curcuminoid)-eudragit polymer ratio. In some embodiments, the ratio of curcumin and/or curcuminoid to eudragit is 1:0.1, 1:0.5, 1:1, 1:2, 1:3, 1:4, 1:5, 1:6, 1:7, 1:8, 1:9, 1:10, 1:15, 1:25 or 1:50.

Other parameters can also be altered to change the size of the particles, including the amount of energy used during sonication and total sonication time. For example, particle size can range from approximately 10 nm to 5000 nm, depending on the solvent and surfactant used during the particle formation process, as well as other experimental parameters, such as shown in FIG. 2. In some embodiments, the particles can be between approximately 10 nm and 50 nm. In some embodiments, the particles can be between approximately 51 nm and 100 nm. In some embodiments, the particles can be between approximately 101 nm and 200 nm. In some embodiments, the particles can be between approximately 201 nm and 300 nm. In some embodiments, the particles can be between approximately 301 nm and 400 nm. In some embodiments, the particles can be between approximately 401 nm and 500 nm. In some embodiments, the particles can be between approximately 501 nm and 1000 nm. In some embodiments, the particles can be between approximately 1001 nm and 2000 nm. In some embodiments, the particles can be between approximately 2001 nm and 3000 nm. In some embodiments, the particles can be between approximately 3001 nm and 4000 nm. In some embodiments, the particles can be between approximately 4001 nm and 5000 nm. In some embodiments, particles can be between approximately 10 nm and 500 nm. In some embodiments, the particles can be between approximately 10 nm and 200 nm. In some embodiments, the particles can be between approximately 201 nm and 401 nm. In some embodiments, the particles can be between approximately 210 nm and 350 nm.

In some aspects, the curcumin or curcuminoid, either alone or in combination, can be formulated by techniques including, but not limited to, nano/micro precipitation, which can be carried out by methods such as sonication, emulsification, solvent titration, milling, spray drying, solid dispersion, hot-melt extrusion, freeze drying methods, or Supercritical Fluid Technology.

Figure 7:
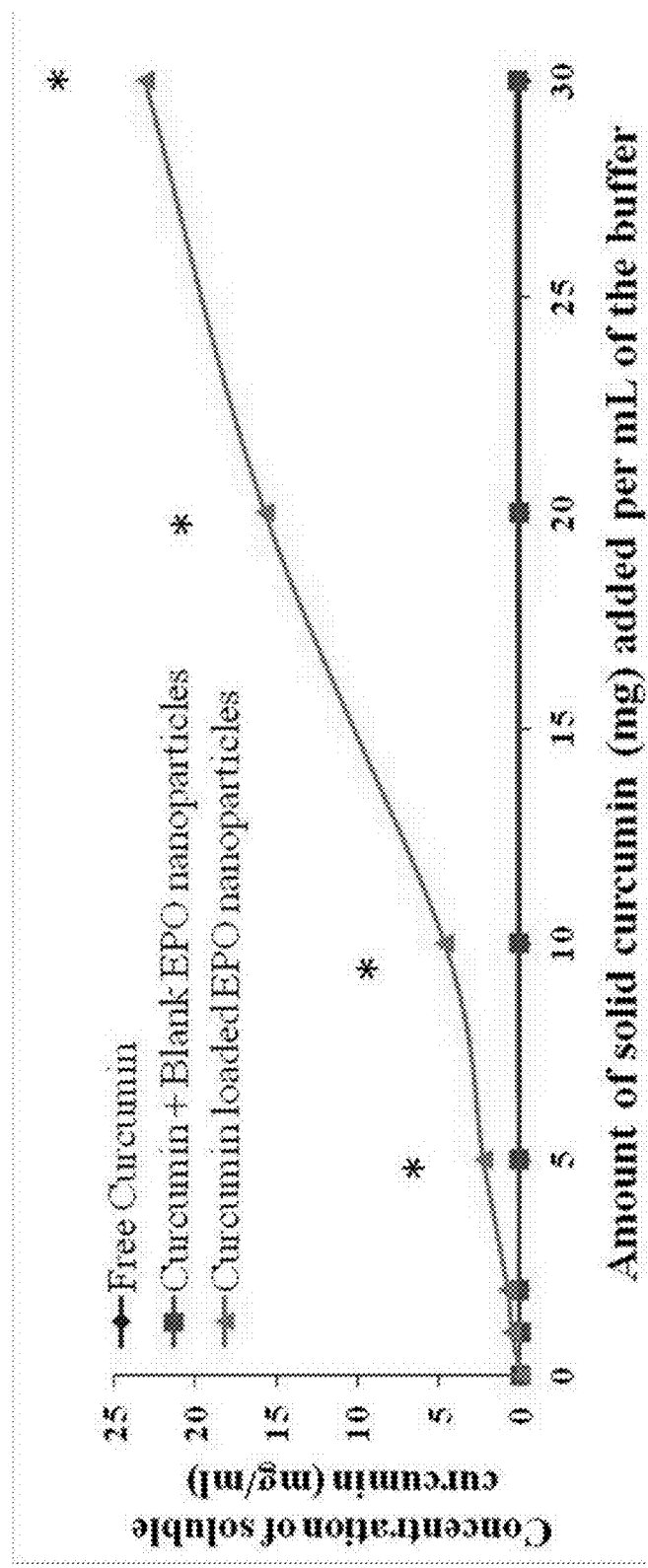
FIG. 7 presents a graph of the kinetic solubility of curcumin in the form of (i) free curcumin, (ii) a physical mixture of blank Eudragit® EPO nanoparticles and free curcumin, and (iii) nanoparticles loaded with curcumin-Eudragit® EPO complexes, according to certain aspects of the present invention, which were dispersed in 1 ml pH 1.2 buffer and incubated at 37 C for 4 hrs with 100 rpm shaking, the curcumin dissolved after 4 hours being spectrophotmetrically analyzed from different samples, with the data representing mean±standard deviation (n=3), and the "*" indicating results that are statistically significant (P<0.05) using a Student t-test.

In some aspects, blank nanoparticles or microparticles lacking curcumin can be used to determine the relative solubility and bioavailability of curcumin by comparing them with particles containing curcumin-eudragit complexes. For example, blank nanoparticles can be produced alongside nanoparticles containing curcumin-eudragit complexes according the methods described above, except that curcumin will not be included in the formulation of the blank nanoparticles. As illustrated in FIG. 7, a higher concentration of nanoparticles loaded with curcumin-Eudragit® EPO complexes were soluble at pH 1.2, compared to blank particles.

In some aspects, therapeutically effective curcumin formulations can comprise an adjuvant that delays or inhibits curcumin metabolism. In some cases, compounds that inhibit P-glycoprotein and glucuronidation can be used to effectively inhibit curcumin metabolism. For example, piperine can be included in the formulation of a composition comprising curcumin-eudragit complexes of the present invention to enhance the therapeutic effects of curcumin. Piperine is an alkaloid that can be extracted from black pepper. It is also known as piperidine, piperoylpiperidine, or by its chemical name, 5-(3,4-methylenedioxyphenyl)-2,4-pentadienoyl-2-piperidine. Piperine inhibits the action of certain enzymes involved in the metabolism and transport of xenobiotics and metabolites, and enzymes involved in drug metabolism (e.g., CYP3A4 and P-glycoprotein). By inhibiting drug metabolism, piperine may increase the bioavailability of various compounds and alter the effectiveness of some medications. For example, piperine may enhance the bioavailability of curcumin by 2000% in humans. Delaying the metabolism of curcumin using piperine enhances its therapeutic effects by enabling it to persist longer in a patient's body or penetrate more deeply into target tissues. In some embodiments, the dose of piperine used in the present invention can be at least about 2.5 mg/day. In some embodiments, the dose of piperine can be between from about 1 to about 100 mg/day, or from about 10 to about 20 mg/day. In some embodiments, the source is *piper longum* derived from black pepper, which comprises at least about 90% piperine.

In some aspects, the formulation of curcumin-eudragit complexes of the present invention can comprise other adjuvants to enhance the therapeutic effects of curcumin, including but not limited to, genistein, EGCG (epigallocatechin-3-gallate), vanillin, gingerol, or any combinations thereof. In other aspects, the formulation of a composition comprising curcumin-eudragit complexes can further comprise other excipients or inactive components to enhance the therapeutic effects of curcumin, including but not limited to, a-lipoic acid, omega3/6 fatty acids, fish oil, vitamin B1, vitamin B6, vitamin D, vitamin B12, folate, vitamin C and/or vitamin E, or any combinations thereof. In other aspects, the formulation of a composition comprising curcumin-eudragit complexes can further comprise other therapeutic drugs such as aspirin, salicylic acid, chemotherapeutic drugs, anti-inflammatory drugs, ant-Alzheimer's disease drugs and thereof. In another aspect, the formulation of a composition comprising curcumin-eudragit complexes can further comprise other components to enhance the therapeutic effects of curcumin, including but not limited to, cream bases and emulsifiers such as light liquid paraffin, PEG, water washable bases such as cetyl alcohol, stearic acid, stearyl alcohol, glycerol monostearate, lanolin, glycerin and others and solid emulsifiers/nonionic surfactants such as Acconon, polyethylene glycol (PEG 200), glyceryl monosterate (GMS), polyethylene glycol (PEG 400) and Cetyl alcohol (CA) and Tween 80, preservatives such as methyl, ethyl or propyl parabens or bronidox, emollient such as Isopropyl myristate for ready absorption into the skin, collagen for maintaining the skin moisture and to give firmness, other flavoring agents such as lavender oil and antiseptic agents such as 2-phenyl ethanol. In another aspect, the formulation of a composition comprising curcumin-eudragit complexes invention can further comprise pharmaceutically, nutraceutically or dietically acceptable anti-inflammatory, anti-psoriatic, antioxidant, anti allergic, antiviral, antibacterial, anti-cancer, anti-neurodegeneration, and anti-angiogenic agents.

Figure 9:
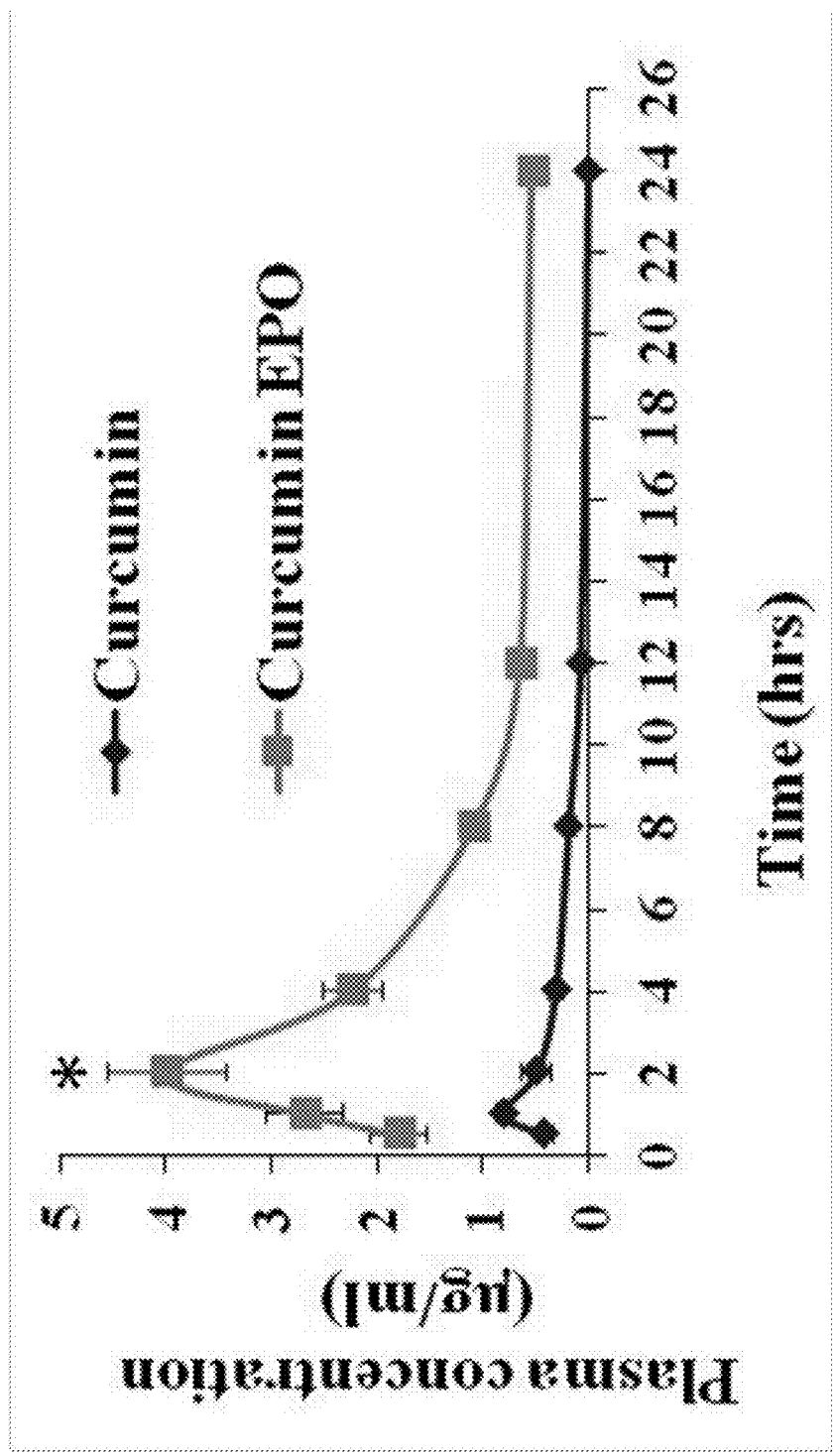
FIG. 9 presents a graph measuring the oral availability of curcumin in mice, according to certain aspects of the present invention, with free curcumin (150 mg/kg) or the equivalent amount of curcumin-Eudragit® EPO complexes being orally administered to mice, and blood samples being collected from mice at different time points, and curcumin extracted from the plasma and analyzed via by HPLC with UV absorption at 420 nm.

In some aspects, the invention provides a method of treating patients for diseases such as cancer, neurodegeneration, inflammation, and immunodeficiency comprising the administration of a composition comprising curcumin-eudragit complexes having enhanced bioavailability. The curcumin-eudragit complexes of the present invention can enhance the bioavailability of curcumin up to 20,000 times or even more compared to free curcumin. In some aspects, the solubility of the curcuminoid component of the medicament preparation is enhanced between about 10 and about 100 times, in some aspects between about 100 and about 500 times, in some aspects between about 500 and about 1000 times, in some aspects between about 1000 and about 5000 times, in some aspects between about 5000 and 10000 times, in some aspects between about 10000 and 15000 times, and in some aspects between about 15000 and 20000 times. As shown in FIG. 9, the presence of a eudragit enhances the bioavailability of curcumin in the blood of mice, as compared to free curcumin.

In some embodiments, a composition comprising curcumin-eudragit complexes can be taken orally in the form of a of a solid (e.g., tablet or pill), a liquid (e.g., solution, suspension or lotion), or semisolid (e.g., gel, cream or ointment). It some embodiments, these compositions be delivered orally and the components be prepared for ingestion in a manner that makes the composition available in therapeutically effective amounts. As such, they may be prepared as water soluble compositions, delivered in liquid form, lyophilized, encapsulated, or in a manner suitable for time release, delayed release or enteric delivery, or any manner typically used for orally delivered pharmaceuticals, nutraceuticals or vitamins, or combined with foods or other normally ingested products. However, the present invention is not limited to oral delivery, as the compositions set forth herein may also be delivered by nasal spray, inhalation techniques, transdermally, transmucossally, ocularly, by suppository, injected, or by intravenous methods. For example, in other embodiments, the compositions comprising curcumin-eudragit complexes can be injected in to the patient's body systemically, or injected into a specific target tissue. In other embodiments, curcumin-eudragit complexes can be applied topically to the patient's skin to treat specifically an injected area, or generally to provide more widespread or systemic therapy.

Figure 10A:
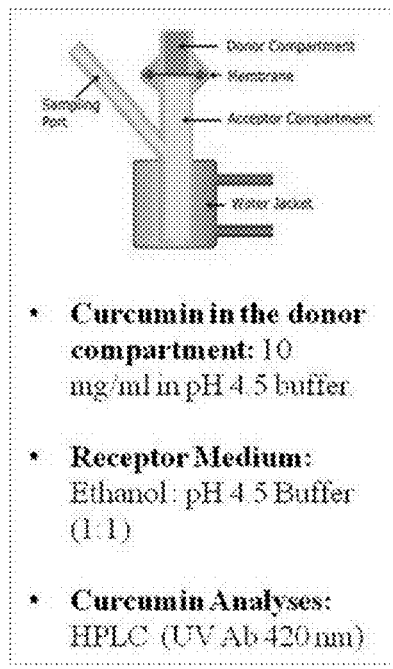
FIG. 10A is a schematic representation of in vitro skin penetration studies performed and referenced in FIG. 10B, according to certain aspects of the present invention, with free curcumin (10 mg/ml) or the equivalent amount of curcumin-Eudragit® EPO complexes being added to the donor chamber in about pH 4.5 buffer, and the amount of curcumin transported across the porcine ear skin (represented as membrane in the schematic) being determined by measuring the amount of curcumin in the acceptor compartment by HPLC with UV absorption at 420 nm.
Figure 10B:
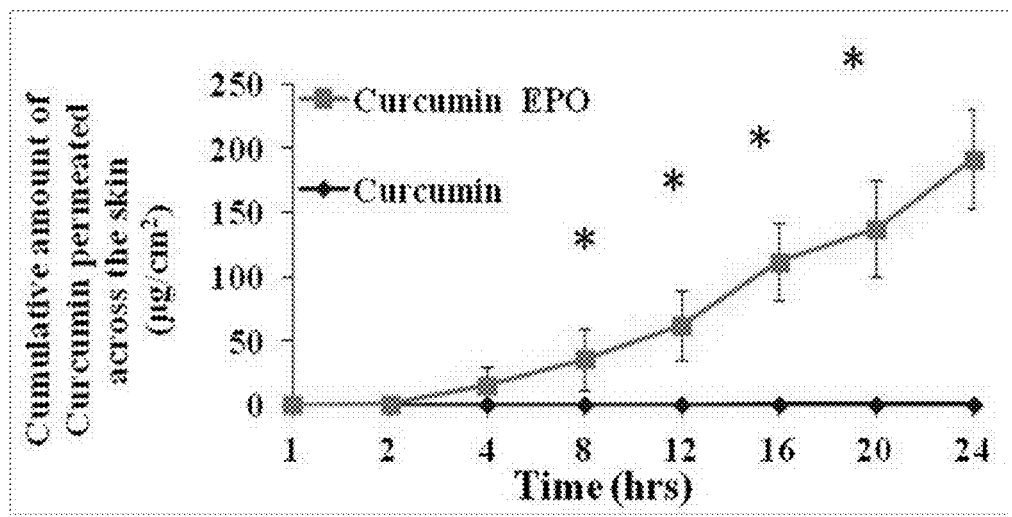
FIG. 10B presents a graph measuring the topical bioavailability of curcumin, according to certain aspects of the present invention, with the in-vitro skin penetration studies being performed using porcine skin, and free curcumin (10 mg/ml) or the equivalent amount of curcumin-Eudragit® EPO complexes being added to the donor chamber in pH 4.5 buffer, the amount of curcumin transported across the skin being determined by HPLC, the amount of curcumin that permeated the skin measured in μg/cm², and the data representing cumulative amounts, with the final time point being 24 hours after the experiment having been initiated.

As shown in FIGS. 10A and 10B, the amount of curcumin transported across the skin increased in the presence of a eudragit, as compared to free curcumin. In other embodiments, the topical formulation of curcumin-eudragit complexes is in a dosage form selected from the group consisting of semisolid dosage forms, ointments, creams, solutions, mouthwash, skin patches, eye drops, medicated sticks, lozenges, pastes, toothpastes, gels, lotions, or suppositories.

In some embodiments, the compositions comprising curcumin-eudragit complexes of the present invention are to be administered at a dosage of from about 0.1 mg/kg/day to about 1 mg/kg/day. In some embodiments, the compositions of the present invention can be administered in a dosage of about 200 mg/day to about 15,000 mg/day. The dosage to be administered can comprise, for example, curcumin in an amount of from about 1.05 to about 85 mg/kg patient body weight, or from about 8.8 to about 13.4 mg/kg body weight, or from about 11.1 to about 111 mg/kg patient body weight, or from about 88.8 to about 133.2 mg/kg patient body weight. The dosage to be administered can also comprise, for example, piperine in an amount of from about 0.01 to about 1.0 mg/kg patient body weight, or from about 0.09 to about 0.9 mg/kg patient body weight or from about 0.09 to about 0.11 mg/kg patient body weight, or from about 0.7 to about 1.1 mg/kg patient body weight.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In addition, the materials, methods, and examples are illustrative only and not intended to be limiting. Other features and advantages of the invention will be apparent from the following detailed description, and from the claims.

EXAMPLES

Example 1

Formation of Nanoparticles Loaded with Curcumin-Eudragit® EPO Complexes

Curcumin and piperine-loaded Eudragit® EPO nanoparticles were prepared using a nanoprecipitation method. During the preparation, either the combination of curcumin and the eudragit polymer, or the combination of curcumin, piperine and the eudragit polymer were dissolved in an organic solvent. The solution was added drop-wise to an aqueous solution containing a surfactant, under sonication. The resulting dispersion was stirred until complete evaporation of the organic solvent. The nanoparticles/microparticles were collected by centrifugation, lyophilized, and stored at 4° C. The amount of curcumin and piperine present in the nanoparticles (loading) was determined by dissolving the particles in ethanol and quantifying the amounts of curcumin (at 262 nm) and piperine (at 342 nm) by HPLC with UV detector. Different formulation and process parameters (e.g., type and concentration of organic solvent or surfactant used, curcumin to eudragit polymer ratio, etc.) were tested in order to optimize the formulation to obtain higher loading and better solubility. The particle size was altered by changing the surfactant type (e.g., Tween-20, Pluronic F68, or polyvinyl alcohol) and the surfactant concentration (1, 2, or 3% w/v) in the preparation. The loading of the curcumin in the formulation (amount of curcumin/mg of formulation) was enhanced by changing the curcumin-eudragit polymer ratio (1:5, 1:3, or 1:2). Other parameters that could be altered to change the size of the particles included the amount of energy used during sonication and total sonication time.

Example 2

Physiochemical Characterization of Nanoparticles Loaded with Curcumin-Eudragit® EPO Complexes Prepared Using Three Different Solvents Nanoparticles loaded with curcumin-Eudragit® EPO complexes were prepared using tween-20 as surfactant in three different solvents (acetone, ethyl acetate and ethanol) and 20 mg of curcumin. Curcumin apparent solubility was measured by dispersing Eudragit® EPO particles equivalent to 2 mg of curcumin in 1 ml of pH 1.2 buffer and incubated at 37 C for 4 hrs with 100 rpm shaking. The curcumin dissolved after 4 hrs was analyzed spectrophotometrically. The curcumin loading and curcumin kinetic solubility data is summarized in Table 2, and illustrated in FIG. 3, whereby the data represents mean±standard deviation (n=3). P.I. stands for Polydispersity Index, which was not measured because of aggregation of the particles. Loading represents µg of curcumin present in 1 mg of Eudragit EPO particles. The "*" indicates results were found statistically significant ($P<0.05$) using a Student t-test.

TABLE 2

Physiochemical characterization of nanoparticles loaded with curcumin-Eudragit ® EPO complexes prepared using three different solvents.

| Sample No. | Solvents | Particle size | P.I. | Curcumin loading (µg/mg) | Curcumin kinetic solubility (mg/ml) |
|---|---|---|---|---|---|
| 1 | Acetone | aggregation | NA | 75.17 ± 0.89* | 0.51 ± 0.02* |
| 2 | Ethyl Acetate | aggregation | NA | 61.70 ± 2.92 | 0.45 ± 0.01 |
| 3 | Ethanol | aggregation | NA | 49.28 ± 1.51 | 0.40 ± 0.02 |

Example 3

Physiochemical Characterization of Nanoparticles Loaded with Curcumin-Eudragit®EPO Complexes Prepared Using Three Different Surfactants Nanoparticles loaded with curcumin-Eudragit® EPO complexes in acetone were prepared using tween-20, Pluronic F-68 or PVA as a surfactant and 20 mg of curcumin. Curcumin apparent solubility was measured by dispersing Eudragit® EPO particles equivalent to 2 mg of curcumin in 1 ml of pH 1.2 buffer and incubated at 37 C for 4 hrs with 100 rpm shaking. The curcumin dissolved after 4 hrs was analyzed spectrophotometrically. The curcumin loading and curcumin kinetic solubility data is summarized in Table 3, and illustrated in FIG. 4, whereby the data represents mean±standard deviation (n=3). P.I. stands for Polydispersity Index. "NA" suggests particle size and polydispersity index were not measured because of aggregation. Loading represents μg of curcumin present in 1 mg of Eudragit® EPO particles. The "*" indicates results were found statistically significant (P<0.05) using a Student t-test.

TABLE 3

Physiochemical characterization of nanoparticles loaded with curcumin-Eudragit ® EPO complexes prepared using three different surfactants.

| Sample No. | Surfactants | Particle Size | P.I. | Curcumin loading (ug/mg) | Curcumin kinetic solubility (mg/ml) |
| --- | --- | --- | --- | --- | --- |
| 1 | Tween-20 | aggregation | na | 75.17 ± 0.89 | 0.51 ± 0.02 |
| 2 | Pluronic F-68 | 343.44 ± 33.27 | 0.57 ± 0.17 | 82.52 ± 2.92 | 0.54 ± 0.01 |
| 3 | PVA | 213.27 ± 12.21 | 0.31 ± 0.12 | 149.24 ± 0.99 * | 0.81 ± 0.01 * |

Example 4

Physiochemical Characterization of Nanoparticles Loaded with Curcumin-Eudragit®EPO Complexes Prepared Using PVA as the Surfactant and Different Amounts of Curcumin Nanoparticles loaded with curcumin-Eudragit® EPO complexes were prepared using different total amounts of curcumin, with PVA as the surfactant. Curcumin apparent solubility was measured in pH 1.2 buffer at 37 C for 4 hrs with 100 rpm shaking. The curcumin dissolved after 4 hrs was analyzed from different samples spectrophotmetrically. Data represents mean±standard deviation (n=3). P.I. stands for Polydispersity Index. Loading represents μg of curcumin present in 1 mg of Eudragit EPO nanoparticles. As provided by the data in Table 4, and illustrated in FIG. 5, at least up to 50 mg of curcumin can be added per 100 mg of the eudragit polymer.

TABLE 4

Physiochemical characterization of nanoparticles loaded with curcumin-Eudragit ® EPO complexes prepared using PVA as the surfactant and different amounts of curcumin.

| Sample No. | Curcumin | Particle size | P.I. | Curcumin loading (ug/mg) |
| --- | --- | --- | --- | --- |
| 1 | 20 mg | 213.27 ± 12.21 | 0.41 ± 0.12 | 149.24 ± 0.99 |
| 2 | 30 mg | 241.32 ± 21.22 | 0.37 ± 0.09 | 175.66 ± 0.88 |
| 3 | 50 mg | 251.32 ± 31.31 | 0.42 ± 0.14 | 278.61 ± 2.72 |

Example 5

Verification of the Formation of Nanoparticles Loaded with Curcumin-Eudragit® EPO Complexes Nanoparticles loaded with curcumin-Eudragit® EPO complexes were prepared with PVA as the surfactant using the aforementioned methods. Free curcumin was dissolved in ethanol, while the curcumin-Eudragit® EPO complexes were dissolved at either pH 1.2 or 4.5, and the samples were incubated at 37 C for 4 hrs with shaking at 100 rpm. The samples were centrifuged and curcumin concentration in the supernatant was analyzed by UV absorbance at 420 nm. The ratio comparing the amount of free curcumin (Mol. Wt. about 368 Da) to that of curcumin-Eudragit® EPO complexes (Mol. Wt.>10 kDa) at pH 1.2 and 4.5 was calculated. As shown in FIG. 2, a ratio around 1 indicates no complex formation, while a ratio less than 1 indicates complex formation between curcumin and Eudragit® EPO.

Example 6

Bioavailability of Curcumin-Eudragit® EPO Complexes in Mice

Nanoparticles loaded with curcumin-Eudragit® EPO complexes were prepared according to the aforementioned methods. Free curcumin (150 mg/kg) or the equivalent amount of curcumin-Eudragit® EPO complexes were orally administered to mice. Blood samples were then collected from the mice at 0.5, 1, 2, 4, 8, 12, and 24 hours after initiation of the experiment. Curcumin was extracted from the blood plasma and analyzed via by HPLC with UV absorption at 420 nm, with the results illustrated in FIG. 9 indicating an increased amount of plasma concentration of the curcumin-Eudragit® EPO complex compared to free curcumin.

Example 7

In-vitro Bioavailability of Curcumin-Eudragit® EPO Complexes Across Porcine Skin Nanoparticles loaded with curcumin-Eudragit® EPO complexes were prepared according to the aforementioned methods, including Example 1. In-vitro skin penetration studies were then performed by topically administering nanoparticles loaded with curcumin-Eudragit® EPO complexes to porcine skin using the apparatus illustrated in FIG. 10A. Free curcumin (10 mg/ml) or the equivalent amount of curcumin-Eudragit® EPO complexes were added to the donor chamber in pH 4.5 buffer, and the amount of curcumin transported across the skin was determined by HPLC. The amount of curcumin that permeated the skin was measured in μg/cm$^2$. Samples were collected at 1, 2, 4, 8, 12, 16, 20, and 24 hours after initiation of the experiment. The cumulative amount of curcumin permeated across the skin measured in μg/cm$^2$ is illustrated in FIG. 10B, which shows the free curcumin amount remained relatively flat around 0 while the curcumin-Eudragit® EPO complex continued to increase the entire 24 hour period.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A curcuminoid composition comprising:
   a curcuminoid-polymer complex comprising at least one curcuminoid component selected from the group consisting of curcumin, demethoxycurcumin, bisdemethoxycurcumin, tetrahydroxycurcumin, Bis-0-Demethyl curcumin (BDMC), or combinations thereof;
   at least one polymer or co-polymer component having a backbone comprising polymethacrylate or methyl methacrylate; and
   surfactant component,
   wherein the curcuminoid component and the polymer or co-polymer component are in the form of the curcuminoid-polymer complex having a plurality of particles with an average particle size between about 10.0 nm and about 5000.0 nm; and
   wherein the curcuminoid-polymer complex is formed by a process comprising:
      dissolving the curmuminoid component and the polymer or co-polymer component in an organic solvent to form a curmuminoid-polymer solution;
      adding the curmuminoid-polymer solution to an aqueous solution having the surfactant to to precipitated the curcuminoid-polymer complex and form a dispersion; and
      removing the organic solvent from the dispersion to collect the curcumoid-polymer complex.

2. The curcuminoid composition of claim 1, wherein the curcuminoid component comprises curcumin.

3. The curcuminoid composition of claim 2, wherein the complex presents an aqueous solubility of the curcumin in an amount greater than about 1 µg/ml.

4. The curcuminoid composition of claim 1, wherein the aqueous solubility is between about 1 µg/ml and about 50 mg/ml.

5. The curcuminoid composition of claim 1, wherein the polymer or co-polymer component is chosen such that the aqueous solubility of the curcuminoid component is greater than about 1 µg/ml at a pH between about 1.0 and about 5.0.

6. The curcuminoid composition of claim 1, wherein the polymer or co-polymer component is chosen such that the aqueous solubility of the curcuminoid component is greater than about 1 µg/ml at a pH between about 5.0 and about 14.0.

7. The curcuminoid composition of claim 1, comprising a first polymer or co-polymer component and a second polymer or co-polymer component, the first polymer or co-polymer forming a first complex and the second polymer or co-polymer forming a second complex, wherein the first polymer or co-polymer component is chosen such that the aqueous solubility of the curcuminoid component of the first complex is greater than about 1 µg/ml at a pH between about 1.0 and about 5.0, and wherein the second polymer or co-polymer component is chosen such that the aqueous solubility of the curcuminoid component of the second complex is greater than about 1 µg/ml at a pH between about 5.5 and about 14.0.

8. The curcuminoid composition of claim 1, wherein a weight ratio of the curcuminoid component to the polymer or co-polymer component is between about 1:0.1 to about 1:50.

9. The curcuminoid composition of claim 1, wherein the complex increases the stability of the curcuminoid component in an aqueous solution compared to free curcumin.

10. The curcuminoid composition of claim 1, further comprising at least one adjuvant.

11. The curcuminoid composition of claim 1, wherein the complex is in the form chosen from a solid, a liquid or a semisolid.

12. A method of forming a plurality of particles comprising a curcuminoid-polymer complex, the method comprising:
   dissolving at least one curcuminoid component and at least one polymer or co-polymer component in an organic solvent to form a solution having the curcuminoid-polymer complex, the polymer component comprising a polymer or co-polymer having a backbone comprising polymethacrylate or methyl methacrylate;
   adding the solution containing the curcuminoid-polymer complex to an aqueous solution containing a surfactant to form the plurality of particles comprising the curcuminoid-polymer complex;
   removing the organic solvent from the aqueous solution comprising the curcuminoid-polymer complex particles;
   separating the curcuminoid-polymer complex particles from the aqueous solution.

13. The method of claim 12, wherein an aqueous solubility of the curcuminoid component of the curcuminoid-polymer complex particles in an aqueous solution is between about 1 µg/ml and about 50 mg/ml at a pH between about 1.0 and about 14.0.

14. The method of claim 12, further comprising adding at least one adjuvant to the organic solvent, wherein the curcuminoid-polymer complex particles comprise the at least one adjuvant.

15. The method of claim 12, further comprising adding a surfactant to the aqueous solution prior to the step of adding the solution containing the curcuminoid-polymer complex to the aqueous solution.

16. The method of claim 12, wherein the curcuminoid component comprises curcumin.

17. A medicament preparation providing enhanced curcuminoid stability, aqueous solubility and/or bioavailability, the medicament preparation comprising:
   at least one curcuminoid component, at least one polymer or co-polymer component and a surfactant in the form of a curcuminoid-polymer complex, the at least one curcuminoid component selected from the group consisting of curcumin, demethoxycurcumin, bisdemethoxycurcumin, tetrahydroxycurcumin, Bis-0-Demethyl curcumin (BDMC), or combinations thereof and the at least one polymer or co-polymer component having a backbone comprising polymethacrylate or methyl methacrylate, wherein the curcuminoid component and the polymer or co-polymer component are provided as the curcuminoid-polymer complex having a plurality of particles with an average particle size between about 10.0 nm and about 5000.0 nm, and wherein the curcuminoid-polymer complex enhances a stability, an aqueous solubility and/or bioavailability of the curcuminoid component compared to a free curcuminoid component when the curcuminoid component and the free curcuminoid component are the same curcuminoid component; and wherein the curcuminoid-polymer complex is formed by a process comprising dissolving the curcuminoid component and the polymer or co-polymer component in an organic solvent to form a curcuminoid-polymer solution, adding the curcuminoid-polymer solution to an aqueous solution having the surfactant to precipitate the curcuminoid-polymer complex and form a dispersion, and removing the organic solvent from the dispersion to collect the curcuminoid-polymer complex.

18. The medicament preparation of claim 17, wherein the curcuminoid component comprises curcumin.

19. The medicament preparation of claim 17, wherein the solubility of the curcuminoid component of the complex in an aqueous solution is between about 1 μg/ml and about 50 mg/ml at a pH between about 1.0 and about 5.0.

20. The medicament preparation of claim 17, wherein the solubility of the curcuminoid component of the complex in an aqueous solution is between about 1 μg/ml and about 50 mg/ml at a pH between about 5.5 and about 14.0.

21. The medicament preparation of claim 17, wherein a weight ratio of the curcuminoid component to the polymer or co-polymer component is between about 1:0.1 to about 1:50.

22. The medicament preparation of claim 17, further comprising at least one surfactant in a concentration between about 1.0% and about 20.0%, weight to volume.

23. The medicament preparation of claim 17, further comprising at least one adjuvant.

24. The medicament preparation of claim 17, wherein the medicament preparation is in the form of a solid, a liquid, or a semisolid.

* * * * *